United States Patent [19]

Walker

[11] Patent Number: 4,650,516
[45] Date of Patent: Mar. 17, 1987

[54] α-HALO-Ω-HALOALKYLAMIDES HERBICIDAL ANTIDOTES

[75] Inventor: Francis H. Walker, Mill Valley, Calif.

[73] Assignee: Stauffer Chemical Co., Westport, Conn.

[21] Appl. No.: 144,703

[22] Filed: Apr. 28, 1980

Related U.S. Application Data

[62] Division of Ser. No. 23,222, Mar. 23, 1979, abandoned.

[51] Int. Cl.⁴ .................... A01N 37/00; A01N 43/40; A01N 43/36; A01N 43/38
[52] U.S. Cl. .......................................... 71/100; 71/94; 71/95; 71/96
[58] Field of Search .......................... 260/340.7, 465.4; 71/100, 105, 94, 95, 96

[56] References Cited

U.S. PATENT DOCUMENTS

| | | | |
|---|---|---|---|
| 2,913,327 | 11/1959 | Jilles et al. | 71/2.7 |
| 3,185,720 | 5/1965 | Jilles et al. | |
| 3,442,945 | 5/1969 | Olin | |
| 3,515,754 | 6/1970 | Mod et al. | 260/465.4 |
| 3,557,184 | 1/1971 | Joepff | 260/465.4 |
| 3,780,090 | 12/1973 | Akiba et al. | |
| 3,803,208 | 4/1974 | Szaba | 260/465.4 |
| 3,966,789 | 6/1976 | Oishi et al. | 260/465.4 |
| 4,021,224 | 5/1977 | Pallos et al. | 71/88 |
| 4,033,756 | 7/1977 | Hoffmann | 71/118 |
| 4,137,070 | 1/1979 | Pallos et al. | 71/100 |

FOREIGN PATENT DOCUMENTS 844937  7/1977  Belgium .

Primary Examiner—Alan Siegel
Attorney, Agent, or Firm—Harry A. Pacini

[57] ABSTRACT

α-Halo-Ω-haloalkylamide compounds have the following formula

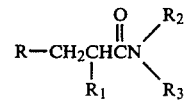

in which
R is selected from the group consisting of chlorine and bromine;
R₁ is selected from the group consisting of chlorine and bromine, provided that it is different from R;
R₂ is selected from the group consisting of hydrogen and methyl; and
R₃ is selected from the group consisting of alkyl having 1 to 10 carbon atoms, alkynyl having 2 to 10 carbon atoms, cyanoalkyl having 2 to 10 carbon atoms, methoxy substituted cyanoalkyl having 2 to 10 carbon atoms, cyanocycloalkyl having 5 to 14 carbon atoms. The compounds are useful as antidotes for the protection of crops from herbicidal injury.

15 Claims, No Drawings

α-HALO-Ω-HALOALKYLAMIDES HERBICIDAL ANTIDOTES

This is a division, of application Ser. No. 23,222, filed Mar. 23, 1979 now abandoned.

BACKGROUND OF THE INVENTION

Uses of Herbicides

An herbicide is a compound which controls or modifies plant growth, e.g., killing, retarding, defoliating, desiccating, regulating, stunting, tillering, stimulating, and dwarfing. "Plant" refers to all physical parts, including seeds, seedlings, saplings, roots, tubers, stems, stalks, foliage, and fruits. "Plant growth" is meant to include all phases of development from seed germination to natural or induced cessation of life.

Herbicides are generally used to control or eradicate weed pests. They have gained a high degree of commercial success because it has been shown that such control increases crop yield and reduces harvesting costs.

Herbicidal effectiveness is dependent upon several variables. One of these is the time or growth related method of application. The most popular methods of application include: pre-plant incorporation into the soil; pre-emergence surface treatment of seeded soil; and post-emergence treatment of the plant and soil.

The most important determinant of herbicidal effectiveness is the susceptibility of the target weed. Certain herbicidal compounds are phytotoxic to some weed species but not to others.

The manufacturer of the herbicide recommends a range of rates and concentrations calculated to maximize weed control. The range of rates varies from approximately 0.01 to 50 pounds per acre, usually from 0.1 to 25 pounds per acre. The actual amount used depends upon several considerations including particular weed susceptibility and overall cost limitations.

Need for Herbicidal Antidotes

Unfortunately, few herbicides are selective exclusively of weed species. Many are toxic to both weeds and the intended crop beneficiary. Therefore, a particular herbicide's use may be proscribed by its injurious effect on the cultivated crop even though it may otherwise provide excellent control of weeds plaguing that crop.

To preserve the beneficial aspects of herbicide use and to mitigate crop damage, many herbicidal antidotes have been prepared. These antidotes reduce or eliminate damage to the crop without substantially impairing the ameliorative effect of the herbicide. See U.S. Pat. No. 4,021,224 and Belgian Pat. No. 846,894.

Although several explanatory theories have been advanced, the precise mechanism by which an antidote reduces herbicidal injury has not been empirically verified. An antidote compound may in fact be a remedy, interferent, protectant, or antagonist. As used herein "antidote" describes the effect of herbicidal phytotoxicity to weed species and reduced or non-phytotoxicity to cultivated crop species.

Prior Art

U.S. Pat. No. 4,021,224 discloses the antidotal properties of haloalkylamide compounds having dichloro halogen substituents for the protection of corn from herbicidal injury.

DESCRIPTION OF THE INVENTION

It has been discovered that haloalkylamide compounds having two differing halogen substituents are superior antidotes for the protection of wheat, barley, and milo from the type of herbicidal injuries such as those caused by thiocarbamates and acetanilides.

These compounds have the following general formula:

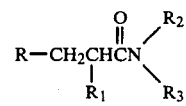

in which
- R is selected from the group consisting of chlorine and bromine;
- $R_1$ is selected from the group consisting of chlorine and bromine, provided that it is different from R;
- $R_2$ is selected from the group consisting of hydrogen and methyl; and
- $R_3$ is selected from the group consisting of alkyl having 1 to 10 carbon atoms, alkynyl having 2 to 10 carbon atoms, cyanoalkyl having 2 to 10 carbon atoms, methoxy substituted cyanoalkyl having 2 to 10 carbon atoms, cyanocycloalkyl having 5 to 14 carbon atoms.

Thiocarbamate herbicides correspond to the following general formula:

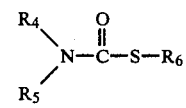

in which
- $R_4$ is selected from the group consisting of 1 to 6 carbon alkyl and 2 to 6 carbon alkenyl;
- $R_5$ is selected from the group consisting of 1 to 6 carbon alkyl, 2 to 6 carbon alkenyl, cyclohexyl and phenyl; or
- $R_4$ and $R_5$ taken together with the nitrogen atom to which they are attached form an alkylene ring; and
- $R_6$ is selected from the group consisting of 1 to 6 carbon alkyl, 1 to 6 carbon haloalkyl, 5 to 10 carbon alkylene ring, phenyl and benzyl. See U.S. Pat. Nos. 2,913,327; 3,198,786; 3,185,720; 2,913,324; and 3,846,115.

The thiocarbamates have been shown particularly effective in the control of grassy type weeds which interfere with the cultivation of a wide variety of crops, e.g., barley, corn, lentils, peanuts, peas, potatoes, soybeans, spinach, tobacco and tomatoes.

Acetanilide herbicides correspond to the following general formula:

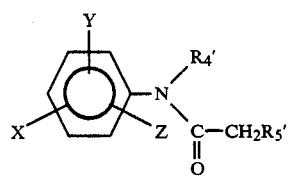

in which

X is selected from the group consisting of hydrogen
and 1 to 4 carbon alkyl;
Y is selected from the group consisting of hydrogen
and 1 to 4 carbon alkyl;
Z is selected from the group consisting of hydrogen
and 1 to 4 carbon alkyl;
R$_4'$ is selected from the group consisting of hydrogen,
1 to 6 carbon alkyl, 2 to 10 carbon alkylalkoxy, 2 to
6 carbon acetoxy, and dioxane; and
R$_5'$ is selected from the group consisting of chlorine,
bromine and iodine. See U.S. Pat. Nos. 3,442,945,
3,937,730 and 3,940,259.

The herbicidal activity of the acetanilides is similar to
that of the thiocarbamates.

The terms "alkyl," "alkenyl," and "alkynyl" as used
herein are intended to include both straight and
branched chain groups. All carbon atom ranges are
intended to be inclusive of both upper and lower limits.

The present invention includes a two-part herbicidal
system consisting of
(a) an antidotally effective amount of a compound of
the formula

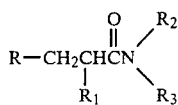

in which
R is selected from the group consisting of chlorine
and bromine;
R$_1$ is selected from the group consisting of chlorine
and bromine, provided that it is different from R;
R$_2$ is selected from the group consisting of hydrogen and methyl; and
R$_3$ is selected from the group consisting of alkyl
having 1 to 10 carbon atoms, alkynyl having 2 to
10 carbon atoms, cyanoalkyl having 2 to 10 carbon atoms, methoxy substituted cyanoalkyl having 2 to 10 carbon atoms, cyanocycloalkyl having 5 to 14 carbon atoms; and
(b) an herbicidally effective amount of a thiocarbamate of the formula

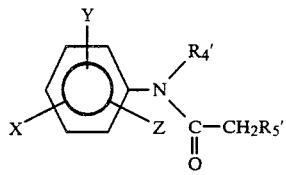

in which
R$_4$ is selected from the group consisting of 1 to 6
carbon alkyl and 2 to 6 carbon alkenyl;
R$_5$ is selected from the group consisting of 1 to 6
carbon alkyl, 2 to 6 carbon alkenyl, cyclohexyl
and phenyl; or
R$_4$ and R$_5$ taken together with the nitrogen atom to
which they are attached form an alkylene ring;
and
R$_6$ is selected from the group consisting of 1 to 6
carbon alkyl, 1 to 6 carbon haloalkyl, 5 to 10
carbon alkylene ring, phenyl and benzyl.

The present invention includes a two-part herbicidal
system consisting of
(a) an antidotally effective amount of the compound
of the formula

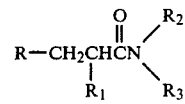

in which
R is selected from the group consisting of chlorine
and bromine;
R$_1$ is selected from the group consisting of chlorine
and bromine, provided that it is different from R:
R$_2$ is selected from the group consisting of hydrogen and methyl; and
R$_3$ is selected from the group consisting of alkyl
having 1 to 10 carbon atoms, alkynyl having 2 to
10 carbon atoms, cyanoalkyl having 2 to 10 carbon atoms, methoxy substituted cyanoalkyl having 2 to 10 carbon atoms, cyanocycloalkyl having 5 to 14 carbon atoms; and
(b) an herbicidally effective amount of an acetanilide
of the formula

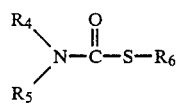

in which
X is selected from the group consisting of hydrogen and 1 to 4 carbon alkyl;
Y is selected from the group consisting of hydrogen and 1 to 4 carbon alkyl;
Z is selected from the group consisting of hydrogen and 1 to 4 carbon alkyl;
R$_4'$ is selected from the group consisting of hydrogen, 1 to 6 carbon alkyl, 2 to 10 carbon alkylalkoxy, 2 to 6 carbon acetoxy, and dioxane; and
R$_5'$ is selected from the group consisting of chlorine, bromine and iodine.

This invention also includes soil treated with the
herbicidal system consisting of
(a) an antidote compound of the formula

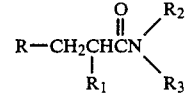

in which
R is selected from the group consisting of chlorine
and bromine;
R$_1$ is selected from the group consisting of chlorine
and bromine, provided that it is different from R;
R$_2$ is selected from the group consisting of hydrogen and methyl; and
R$_3$ is selected from the group consisting of alkyl
having 1 to 10 carbon atoms, alkynyl having 2 to
10 carbon atoms, cyanoalkyl having 2 to 10 carbon atoms, methoxy substituted cyanoalkyl having 2 to 10 carbon atoms, cyanocycloalkyl having 5 to 14 carbon atoms; and
(b) a thiocarbamate herbicide of the formula

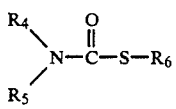

in which
- $R_4$ is selected from the group consisting of 1 to 6 carbon alkyl and 2 to 6 carbon alkenyl;
- $R_5$ is selected from the group consisting of 1 to 6 carbon alkyl, 2 to 6 carbon alkenyl, cyclohexyl and phenyl; or
- $R_4$ and $R_5$ taken together with the nitrogen atom to which they are attached form an alkylene ring; and
- $R_6$ is selected from the group consisting of 1 to 6 carbon alkyl, 1 to 6 carbon haloalkyl, 5 to 10 carbon alkylene ring, phenyl and benzyl.

This invention includes soil treated with the herbicidal system consisting of (a) an antidote compound of the formula

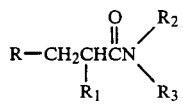

in which
- R is selected from the group consisting of chlorine and bromine;
- $R_1$ is selected from the group consisting of chlorine and bromine;
- $R_2$ is selected from the group consisting of hydrogen and methyl; and
- $R_3$ is selected from the group consisting of alkyl having 1 to 10 carbon atoms, alkynyl having 2 to 10 carbon atoms, cyanoalkyl having 2 to 10 carbon atoms, methoxy substituted cyanoalkyl having 2 to 10 carbon atoms, cyanocycloalkyl having 5 to 14 carbon atoms, and dioxane; and (b) an acetanilide herbicide of the formula

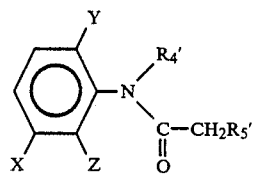

in which
- X is selected from the group consisting of hydrogen and 1 to 4 carbon alkyl;
- Y is selected from the group consisting of hydrogen and 1 to 4 carbon alkyl;
- Z is selected from the group consisting of hydrogen and 1 to 4 carbon alkyl;
- $R_4'$ is selected from the group consisting of hydrogen, 1 to 6 carbon alkyl, 2 to 10 carbon alkyl, alkoxy, 2 to 6 carbon acetoxy, and dioxane; and
- $R_5'$ is selected from the group consisting of chlorine, bromine and iodine.

Preparation

The thiocarbamates of the present compositions can be prepared by the procedures described in the commonly assigned and expired U.S. Pat. Nos. 2,913,324 and 2,913,327.

The acetanilides of the present compositions can be prepared by the procedures described in U.S. Pat. Nos. 3,442,945, 3,780,090, 3,937,730 and British Pat. No. 1,455,471.

The compounds of this invention represented by the above formula can be prepared by several different procedures depending upon the starting materials. The following procedure is a general method of preparation.

A bromine substituted acid chloride reactant is prepared by dissolving an acid chloride and a slight molar excess of N-bromosuccinimide in carbon tetrachloride in the presence of an aqueous hydrogenbromide catalyst. The mixture is heated at reflux for 4 hours. It is then cooled and filtered. The filtrate is vacuum distilled to isolate the bromine substituted acid chloride product. This method of preparation is described by Harpp et al., *Journal of Organic Chemistry*, Volume 40, at 3420–27 (1975).

Haloalkylamide compounds are prepared by slowly adding the acid chloride described above to a mixture of a suitable amine, a 50% sodium hydroxide solution, water, and methylene chloride which is being rapidly stirred at a temperature under 35° C. The mixture is subsequently washed and recovered from the organic phase.

The reactant, (used in Examples 1, 2, 3 and 4) 2-bromo-3-chloropropionyl chloride, was prepared in the following manner. Fifty grams (g) or 0.39 mole of 3-chloropropionyl chloride, 83.3 g (0.47 mole) N-bromosuccinimide, carbon tetrachloride, and 10 drops of 48% hydrogen bromide were mixed together. After refluxing for 4 hours at 75° C., the solution was filtered.

The solvent was evaporated by vacuum distillation, leaving 75.1 g. The residue was placed in a 100 milliliter (ml) microware distillation flask for redistillation. The first fraction taken having the boiling point range from 25° to 50° C. yielded 1.2 g of the product ($n_D^{30}$=1.4817).

The second fraction with the boiling point range of 52°–58° C. yielded 50.4 g of the product ($n_D^{30}$=1.4997). The product 2-bromo-3-chloropropionyl chloride was confirmed by gas chromatography.

The following are specific examples of the preparation according to these general methods of compounds typical of this invention. (The compound numbers are those which appear in Table I and IV.)

EXAMPLE 1

Preparation of N-t-butyl-2-bromo-3-chloropropionamide (Compound No. 1)

A mixture of 4.4 g (0.06 mole) t-butyl amine, 4.0 g (0.05 mole) 50% sodium hydroxide, water, and methylene chloride was placed in an ice bath. 2-Bromo-3-chloroproionyl (10.3 g or 0.05 mole) was slowly added to the mixture under constant stirring. The mixture was washed with 50 ml of water and filtered. This yielded 4.8 g of a white solid (m.p. 163°–168° C.). The organic layer was separated and stripped to yield a wet solid. This was recrystallized in ethanol and water, yielding an additional 2.1 g of the product N-t-butyl-2-bromo-3-chloropropionamide (m.p. 161°–167° C.).

EXAMPLE 2

Preparation of
N-(1,1-dimethylacetonitrilo)-2-bromo-3-chloropropionamide (Compound No. 18)

2-Bromo-3-chloropropionyl chloride (10.3 g or 0.05 mole) was slowly added with constant stirring to a mixture of 4.2 g (0.05 mole) α-aminoisobutyronitrile, 4.0 g (0.05 mole) 50% sodium hydroxide, water, and methylene chloride. During the addition the mixture was kept in an ice bath to keep it within a 24°–35° C. temperature range. Filtration yielded 2.6 g of white solid (m.p. 125°–127° C.). Evaporation of the filtrate yielded 7.2 g of yellow solid product. This was recrystallized in ethanol and water to yield an additional 4.0 g of N-(1,1-dimethylacetonitrilo)-2-bromo-3-chloropropionamide (m.p. 115°–120° C.). The structure was confirmed by nuclear magnetic resonance.

EXAMPLE 3

Preparation of
N-(1-cyclopentanecarbonitrilo)-2-bromo-3-chloropropionamide (Compound No. 23)

Preparation of Reactant

Ammonium chloride (48.2 g or 0.90 mole), 73.6 g (0.87 mole) cyclopentanone and ether were combined in a 1000 ml flask. The mixture was cooled to 5° C. Potassium cyanide (59.6 g or 0.92 mole) on water was added drop-wise to the mixture. The mixture was stirred for several hours. After filtration and separation from the water portion, the solution was washed three times with 75 ml of ether. After drying over magnesium sulfate, it was filtered into a one liter round-bottomed flask. Hydrogen chloride gas was passed into the flask. A precipitate formed which was recovered by suction filtration. It was washed with ether and vacuum dried. The product consisted of 26.2 g of 1-aminocyclopentane-carbonitrile as a hydrochloride salt (decomposition above 150° C.).

2-Bromo-3-chloropropionyl chloride (8.0 g or 0.04 mole) was slowly added to a mixture of 7.3 g (0.05 mole) of the hydrochloride salt of 1-aminocyclopentane-carbonitrile, 6.4 g (0.08 mole) of 50% sodium chloride, water, and methlene chloride in an ice bath. The solution was washed with 50 ml of water. There were 7.7 g of product after stripping. It was recrystallized from a water and ethanol solution. The first recrystallization yielded 2.8 g of N-(1-cyclopentanecarbonitrilo)-2-bromo-3-chloropropionamide (m.p. 122°–127° C.). Structure was confirmed by nuclear magnetic resonance.

Other examples of the compounds prepared according to these methods are found in Table I.

TABLE I

α-Halo-Ω-haloalkylamides Herbicidal Antidotes

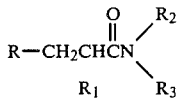

| Compound No. | R | $R_1$ | $R_2$ | $R_3$ | Name | Physical Constant |
|---|---|---|---|---|---|---|
| 1 | Cl | Br | H | —C(CH$_3$)$_3$ | N—t-butyl-2-bromo-3-chloropropionamide | m.p. 163–167° C. |
| 2 | Cl | Br | H | —C(CH$_3$)(CH$_2$CH$_3$)(CH$_3$) | N—t-pentyl-2-bromo-3-chloropropionamide | m.p. 148–151° C. |
| 3 | Cl | Br | H | —CH(C$_2$H$_5$)$_2$ | N—(1-ethylpropyl)-2-bromo-3-chloropropionamide | m.p. 153–155° C. |
| 4 | Cl | Br | CH$_3$ | —CH$_2$C≡CH | N—methyl-N—(2-propynyl)-2-bromo-3-chloropropionamide | $n_D^{30}$ 1.5258 |
| 5 | Cl | Br | H | —CHC≡CH (CH$_3$) | N—(1-methyl-2-propynyl)-2-bromo-3-chloropropionamide | m.p. 124–127° C. |
| 6 | Cl | Br | CH$_3$ | —CHC≡CH (CH$_3$) | N—methyl-N—(1-methyl-2-propynyl)-2-bromo-3-chloropropionamide | dark oil |
| 7 | Cl | Br | H | —CC≡CH (CH$_3$)(CH$_3$) | N—(1,1-dimethyl-2-propynyl)-2-bromo-3-chloropropionamide | decomposition above 115° C. |
| 8 | Br | Cl | H | —CC≡CH (CH$_3$)(CH$_3$) | N—(1,1-dimethyl-2-propynyl)-2-chloro-3-bromopropionamide | m.p. 98–100° C. |
| 9 | Cl | Br | H | —CC≡CCH$_3$ (CH$_3$)(CH$_3$) | N—(1,1-dimethyl-2-butynyl)-2-bromo-3-chloropropionamide | m.p. 105–110° C. |

TABLE I-continued

α-Halo-Ω-haloalkylamides Herbicidal Antidotes

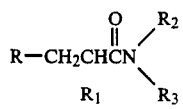

| Compound No. | R | $R_1$ | $R_2$ | $R_3$ | Name | Physical Constant |
|---|---|---|---|---|---|---|
| 10 | Br | Cl | H | —C(CH$_3$)(CH$_3$)C≡CCH$_3$ | N—(1,1-dimethyl-2-butynyl)-2-chloro-3-bromopropionamide | $n_D^{30}$ 1.5137 |
| 11 | Cl | Br | H | —C(C$_2$H$_5$)(CH$_3$)C≡CH | N—(1-methyl-1-ethyl-2-propynyl)-2-bromo-3-chloropropionamide | m.p. 103–104° C. |
| 12 | Br | Cl | H | —C(CH$_3$)(C$_2$H$_5$)C≡CH | N—(1-ethyl-1-methyl-2-propynyl)-2-chloro-3-bromopropionamide | m.p. 93–96° C. |
| 13 | Cl | Br | H | —C(C$_2$H$_5$)(C$_2$H$_5$)C≡CH | N—(1,1-diethyl-2-propynyl)-2-bromo-3-chloropropionamide | m.p. 98–100° C. |
| 14 | Br | Cl | H | —C(C$_2$H$_5$)(C$_2$H$_5$)C≡CH | N—(1,1-diethyl-2-propynyl)-2-chloro-3-bromopropionamide | waxy solid |
| 15 | Cl | Br | H | —C(CH$_3$)(CH$_3$)C≡CC$_2$H$_5$ | N—(1,1-dimethyl-2-pentynyl)-2-bromo-3-chloropropionamide | m.p. 82–87° C. |
| 16 | Cl | Br | H | —C(CH$_3$)(CH(CH$_3$)$_2$)C≡CH | N—(1-methyl-1-isopropyl-2-propynyl)-2-bromo-3-chloropropionamide | m.p. 106–107° C. |
| 17 | Br | Cl | H | —C(CH$_3$)(CH$_3$)C≡N | N—(1,1-dimethylacetonitrilo)-2-chloro-3-bromopropionamide | semi-solid |
| 18 | Cl | Br | H | —C(CH$_3$)(CH$_3$)C≡N | N—(1,1-dimethylacetonitrilo)-2-bromo-3-chloropropionamide | m.p. 115–120° C. |
| 19 | Cl | Br | CH$_3$ | —CH(CH$_3$)C≡N | N—methyl-N—(1-cyano-1-methylethyl)-2-bromo-3-chloropropionamide | $n_D^{30}$ 1.5208 |
| 20 | Br | Cl | H | —C(CH$_2$OCH$_3$)(CH$_3$)C≡N | N—(1-cyano-1-methyl-2-methoxyethyl)-2-chloro-3-bromopropionamide | $n_D^{30}$ 1.4998 |
| 21 | Cl | Br | H | —C(CH$_3$)(CH(CH$_3$)$_2$)C≡N | N—(1-cyano-1',2'-dimethylpropyl)-2-bromo-3-chloropionamide | m.p. 102–112° C. |
| 22 | Cl | Br | H | —C(CH$_2$OCH$_3$)(CH$_3$)C≡N | N—(1-cyano-1-methyl-2-methoxyethyl)-2-bromo-3-chloropropionamide | $n_D^{30}$ 1.4992 |

TABLE I-continued

α-Halo-Ω-haloalkylamides Herbicidal Antidotes

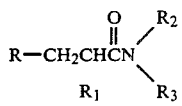

| Compound No. | R | $R_1$ | $R_2$ | $R_3$ | Name | Physical Constant |
|---|---|---|---|---|---|---|
| 23 | Cl | Br | H | (1-cyclopentanecarbonitrile) | N—(1-cyclopentanecarbonitrilo)-2-bromo-3-chloropropionamide | m.p. 122–127° C. |
| 24 | Cl | Br | H | (1-cyclopentylacetonitrile) | N—(1-cyclopentylacetonitrilo)-2-bromo-3-chloropropionamide | $n_D^{30}$ 1.5131 |
| 25 | Cl | Br | H | (1-cyanocyclohexyl) | N—(1-cyanocyclohexyl)-2-bromo-3-chloropropionamide | m.p. 149–152° C. |
| 26 | Br | Cl | H | (1-cyanocyclohexyl) | N—(1-cyanocyclohexyl)-2-chloro-3-bromopropionamide | m.p. 90–100+° C. decomposed |
| 27 | Cl | Br | H | (1-cyano-4-methylcyclohexyl) | N—(1-cyano-4-methylcyclohexyl)-2-bromo-3-chloropropionamide | decomposition above 80° C. |
| 28 | Br | Cl | H | (1-cyano-4-methylcyclohexyl) | N—(1-cyano-4-methylcyclohexyl)-2-chloro-3-bromopropionamide | waxy solid |
| 29 | Cl | Br | H | (1-cyano-4-ethylcyclohexyl) | N—(1-cyano-4-ethylcyclohexyl)-2-bromo-3-chloropropionamide | m.p. 129–132° C. |
| 30 | Cl | Br | H | (1-cyano-4-t-butylcyclohexyl) | N—(1-cyano-4-t-butylcyclohexyl)-2-bromo-3-chloropropionamide | m.p. 147–151° C. |
| 31 | Cl | Br | H | (1-cyano-4-t-pentylcyclohexyl) | N—(1-cyano-4-t-pentyl-cyclohexyl)-2-bromo-3-chloropropionamide | semi-solid |
| 32 | Cl | Br | H | (1-cyanocycloheptyl) | N—(1-cyanocycloheptyl)-2-bromo-3-chloropropionamide | m.p. 136–140° C. |

TABLE I-continued

α-Halo-Ω-haloalkylamides Herbicidal Antidotes

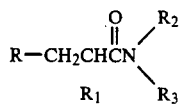

| Compound No. | R | R₁ | R₂ | R₃ | Name | Physical Constant |
|---|---|---|---|---|---|---|
| 33 | Cl | Br | H | (cyanocyclooctyl group) | N—(1-cyanocyclooctyl)-2-bromo-3-chloropropionamide | m.p. 132–134° C. |
| 34 | Br | Cl | H | (cyanocyclooctyl group) | N—(1-cyanocyclooctyl)-2-chloro-3-bromopropionamide | m.p. 117–120° C. |

Testing

Stock solutions of the herbicides were prepared by diluting the requisite amount of each herbicide in water. The solution concentrations and application rates and times are summarized in Table II.

TABLE II

Herbicide Stock Solutions

| Herbicide Name | Concentration Herbicide (mg) | Water (ml) | Application ml/flat∼ | lb/acre | Method* |
|---|---|---|---|---|---|
| VERN | 427 | 400 | 5 | 1.00 | PPI |
| S—propyldipropyl-thiocarbamate | 533 | 400 | 5 | 1.25 | PPI |
|  | 2560 | 400 | 5 | 6.00 | PPI |
| EPTC S—ethyl-N,N—dipropyl-thiocarbamate | 2225 | 350 | 5 | 6.00 | PPI |
| RON | 1280 | 400 | 5 | 3.00 | PPI |
| S—ethyl-N—cyclohexyl-thiocarbamate | 1456 | 350 | 5 | 4.00 | PPI |
| LAS | 1000 | 80 | 2 | 3.00 | PES |
| 2-chloro-2',6'-diethyl-N—(methoxymethyl) acetanilide | 1333 | 80 | 2 | 4.00 | PES |
| SUT | 3200 | 500 | 5 | 6.00 | PPI |
| S—ethyl diisobutyl-thiocarbamate |  |  |  |  |  |
| ANT | 299 | — | 2 | 3.00 | PES |
| N—(2'-methylcarbethyl)-2,6-diethyl chloro-acetamide |  | 50 acetone |  |  |  |

*See the Key to Table IV for explanation of symbols for time related methods of application Stock solutions of each antidote compound were prepared at the desired concentrations by diluting the requisite amounts of each antidote in acetone. The concentrations and rates for each method of application are summarized in Table III.

TABLE III

Antidote Stock Solutions
Antidote: α-Halo-Ω-haloalkylamide

| Concentration | | Application | | |
|---|---|---|---|---|
| Antidote (mg) | Acetone (ml) | ml/flat∼ | lb/acre | Method* |
| 95 | 15 | 0.30 | 1.00 | IF |
| 95 | 15 | 1.50 | 5.00 | IF |
| 100 | 25 | 5.00 | 5.00 | PPI |
| 40 | 25 | 5.00 | 2.00 | PPI |
| 100 | 25 | 1.00 | 1.00 | PPI |
| 40 | 25 | 1.25 | 0.50 | PPI |
| 16 | 40 | 2.50 | 0.25 | PPI |
| High Dilutions Stock Solution A: | | | | |
| 50 | 100 | | | |
| 10 (ml) A | 90 | 4.00 | 0.05 | PPI |
| 10 (ml) A | 90 | 2.00 | 0.025 | PPI |
| 10 (ml) A | 90 | 1.00 | 0.0125 | PPI |
| Stock Solution B: | | | | |
| 10 (ml) A | 90 | | | |
| 10 (ml) B | 90 | 2.00 | 0.0025 | PPI |
| 40 | 20 | 1.00 | 0.50 | PES |
| 40 | 20 | 2.00 | 1.00 | PES |
| 100 | 10 | 2.00 | 5.00 | PES |

*See the Key to Table IV for explanation of symbols for time related methods of application All of the soil used in the tests described herein was loamy sand soil treated with 50 parts per million (ppm) each of cis-N[(trichloromethyl)thio]-4-cyclohexane-1,2-dicarboximide, a fungicide sold as CAPTAN ®, and an 18-18-18 fertilizer, which contains 18% by weight equivalent each of nitrogen, phosphorus pentoxide, and potassium oxide.

For in-furrow (IF) antidote applications planting flats were filled with soil treated by the pre-plant incorporation (PPI) of the herbicide. A one pint sample of soil removed from each flat was retained to cover the seeds after treatment. After leveling and furrowing the soil, seeds of the crop or weed species were planted ½ inch deep. Each flat was divided in half by a wooden barrier. A stock solution of the antidote was atomized directly onto the exposed seeds and soil in the open furrows on one side of the barrier. The seeds in the entire flat were then covered with the previously removed soil. The antidotally untreated sections of flats were compared for observed differences which would indicate lateral movement of the antidote through the soil.

For the pre-plant incorporation method the herbicide and the antidote of each test group were incorporated into the soil as a tank mix using a five gallon rotary mixer.

For the pre-emergence (PES) method of application the antidote and herbicide were sprayed on the soil surface of seeded flats.

All flats were placed on greenhouse benches where temperature was maintained between 70° and 90° F. The flats were watered by sprinkling as needed to assure good plant growth.

Control flats contained crops treated with herbicides only at the various rates and methods of application.

The effectiveness of the antidote was determined by visual comparison of injuries to crops and weeds in the control and test flats to those in untreated flats.

Injury ratings were taken four weeks after application of the antidote by in-furrow or pre-plant incorporation methods.

The treated crops initially screened for diminution of herbicidal injury were milo, wheat, cotton, rice, barley, corn, and soybeans. Those compounds which showed substantial crop injury reduction were further tested at reduced rates. The herbicides and antidote compositions were then screened on at least two weed species. The weed species tested for control included watergrass (*Echinochloa crusgalli*), foxtail (*Setaria viridis*), wild oat (*Avena fatua*), Johnsongrass (*Sorghum halepense*), shattercane (*Sorghum bicolor*), and yellow nutsedge (*Cyperus esculentus*).

KEY TO TABLES IV AND V

Antidotes

Compound numbers in this Table correspond to the numbers and their chemical description in Table I.
Application times:
IF = In-furrow surface application
PPI = Pre-plant incorporation into the soil. This is a tank mix which combined herbicide and antidote unless followed by an asterisk (*) which denotes separate incorporation of herbicide and antidote.
PES = Pre-emergence surface application

Herbicides

VERN = Vernam ®, S-propyl dipropylthiocarbamate, as described in commonly assigned and expire U.S. Pat. No. 2,913,324
EPTC = Eptam ®, S-ethyl-N,N-dipropylthiocarbamate, as described in commonly assigned and expire U.S. Pat. No. 2,913,327
RON = Ro-neet ®, S-ethyl N-ethyl-N-cyclohexylthiocarbamate, as described in commonly assigned U.S. Pat. No. 3,185,720
LAS = Lasso ®, 2-chloro-2',6'-diethyl-N-(methoxymethyl) acetanilide, as described in U.S. Pat. No. 3,442,945
SUT = Sutan ®, S-ethyl diisobutylthiocarbamate, as described in commonly assigned and expire U.S. Pat. No. 2,913,327
ANT = Antor ®, N-(2'-methylcarbethoxy)-2,6-diethyl chloroacetamide, U.S. Pat. No. 3,780,090.

Application Times:
PPI for VERN, EPTC, RON and SUT
PES for LAS and ANT

Rates:
All rates are shown in pounds per acre. The first two horizontal columns represent the initial screen. Compounds showing sufficient antidotal activity in this screen were subsequently tested at lower rates on both crops and weeds.

Injury Ratings:
U = Antidotally Untreated; % Injury 4 weeks after herbicide application.
T = Antidotally Treated; % Injury 4 weeks after treatment with antidote compound.
— = Indicates no change.

TABLE IV

Effectiveness of Herbicidal Antidote

| Antidote Compound No. | Application Rate | Application Time | Herbicide Name | Herbicide Rate | Milo U | Milo T | Wheat U | Wheat T | Cotton U | Cotton T | Rice U | Rice T | Barley U | Barley T | Corn U | Corn T | Soybean U | Soybean T |
|---|---|---|---|---|---|---|---|---|---|---|---|---|---|---|---|---|---|---|
| 1 | 5.00 | IF | VERNAM | 1.00 | 85 | 10 | 80 | 60 | 70 | — | 95 | 40 | 70 | 40 | | | | |
|  | 5.00 | IF | VERNAM | 6.00 | | | | | | | | | | | 90 | 0 | 50 | 70 |
|  | 1.00 | IF | VERNAM | 1.00 | | | | | | | 80 | 50 | | | | | | |
|  | 5.00 | IF | VERNAM | 1.00 | | | | | | | 80 | 40 | | | | | | |
|  | 1.00 | IF | VERNAM | 1.25 | | | | | | | | | 95 | 30 | | | | |
|  | 5.00 | IF | VERNAM | 1.25 | | | | | | | | | 95 | 40 | | | | |
|  | 0.50 | PPI | VERNAM | 1.25 | | | | | | | | | 50 | 20 | | | | |
|  | 1.00 | PPI | VERNAM | 1.25 | | | | | | | | | 50 | 20 | | | | |
|  | 2.00 | PPI | VERNAM | 1.25 | | | | | | | | | 50 | 20 | | | | |
|  | 1.00 | IF | RONEET | 4.00 | 60 | 20 | | | | | | | | | | | | |
|  | 5.00 | IF | RONEET | 4.00 | 60 | 0 | | | | | | | | | | | | |
|  | 5.00 | PES | LASSO | 3.00 | 90 | 15 | 55 | 10 | | | | | | | | | | |
|  | 5.00 | PES | LASSO | 4.00 | | | | | | | | | 80 | 15 | | | | |
| 2 | 5.00 | IF | VERNAM | 1.00 | 80 | 60 | 80 | 40 | 70 | — | 95 | 30 | 70 | 30 | | | | |
|  | 5.00 | IF | VERNAM | 6.00 | | | | | | | | | | | 90 | 30 | 50 | 70 |
|  | 1.00 | IF | VERNAM | 1.00 | | | 80 | 40 | | | | | | | | | | |
|  | 5.00 | IF | VERNAM | 1.00 | | | 80 | 40 | | | | | | | | | | |
|  | 1.00 | IF | VERNAM | 1.00 | | | | | | | 80 | — | | | | | | |
|  | 5.00 | IF | VERNAM | 1.00 | | | | | | | 80 | 50 | | | | | | |
|  | 1.00 | IF | VERNAM | 1.25 | | | | | | | 95 | 40 | 95 | 40 | | | | |
|  | 5.00 | IF | VERNAM | 1.25 | | | | | | | 95 | 40 | 95 | 40 | | | | |
|  | 0.50 | PPI | VERNAM | 1.25 | | | | | | | 50 | 20 | 50 | 20 | | | | |
|  | 1.00 | PPI | VERNAM | 1.25 | | | | | | | | | 50 | 20 | | | | |
|  | 2.00 | PPI | VERNAM | 1.25 | | | | | | | | | 50 | 20 | | | | |
| 3 | 5.00 | IF | VERNAM | 1.25 | 100 | 70 | 95 | 30 | 50 | — | 95 | — | 70 | 10 | | | | |
|  | 5.00 | IF | VERNAM | 6.00 | | | | | | | | | | | 95 | 0 | 50 | 0 |
|  | 1.00 | IF | VERNAM | 1.00 | | | 80 | 55 | | | | | | | | | | |

TABLE IV-continued
Effectiveness of Herbicidal Antidote

| Antidote Compound No. | Application Rate | Application Time | Herbicide Name | Herbicide Rate | % Crop Injury | | | | | | | | | | | | | | |
|---|---|---|---|---|---|---|---|---|---|---|---|---|---|---|---|---|---|---|---|---|
| | | | | | Milo | | Wheat | | Cotton | | Rice | | Barley | | Corn | | Soybean | |
| | | | | | U | T | U | T | U | T | U | T | U | T | U | T | U | T |
| | 5.00 | IF | VERNAM | 1.00 | | | 80 | 30 | | | | | | | | | | |
| | 1.00 | IF | VERNAM | 1.25 | | | | | | | | | 95 | 40 | | | | |
| | 5.00 | IF | VERNAM | 1.25 | | | | | | | | | 95 | 30 | | | | |
| | 0.50 | PPI | VERNAM | 1.25 | | | | | | | | | 50 | — | | | | |
| | 1.00 | PPI | VERNAM | 1.25 | | | | | | | | | 50 | — | | | | |
| | 2.00 | PPI | VERNAM | 1.25 | | | | | | | | | 50 | — | | | | |
| | 5.00 | PES | LASSO | 3.00 | 90 | 80 | 55 | 10 | | | | | | | | | | |
| | 5.00 | PES | LASSO | 4.00 | | | | | | | | | 80 | 15 | | | | |
| 4 | 5.00 | IF | VERNAM | 1.25 | 100 | 30 | 100 | 60 | 50 | 70 | 100 | 80 | 90 | 40 | | | | |
| | 5.00 | IF | VERNAM | 6.00 | | | | | | | | | | | 90 | 0 | 70 | 50 |
| | 1.00 | IF | VERNAM | 1.25 | | | | | | | | | 80 | 40 | | | | |
| | 5.00 | IF | VERNAM | 1.25 | | | | | | | | | 80 | 40 | | | | |
| | 0.50 | PPI | EPTAM | 6.00 | | | | | | | | | | | 70 | — | | |
| | 5.00 | PPI | EPTAM | 6.00 | | | | | | | | | | | 70 | 0 | | |
| | 1.00 | IF | RONEET | 3.00 | 75 | 40 | | | | | | | | | | | | |
| | 5.00 | IF | RONEET | 3.00 | 75 | 40 | | | | | | | | | | | | |
| | 1.00 | PPI | SUTAN | 6.00 | | | | | 50 | 40 | | | | | | | | |
| | 5.00 | PPI | SUTAN | 6.00 | | | | | 50 | — | | | | | | | | |
| 5[1] | 5.00 | IF | VERNAM | 1.25 | 100 | — | 85 | — | 60 | 80 | 100 | — | 80 | — | | | | |
| | 5.00 | IF | VERNAM | 6.00 | | | | | | | | | | | 90 | — | 60 | — |
| | 5.00 | IF | VERNAM | 1.25 | 100 | 95 | 100 | 40 | 60 | — | 100 | — | | | | | | |
| | 5.00 | IF | VERNAM | 6.00 | | | | | | | | | 90 | 70 | 95 | 60 | 60 | 80 |
| | 1.00 | IF | VERNAM | 1.00 | | | 99 | 35 | | | | | | | | | | |
| | 5.00 | IF | VERNAM | 1.00 | | | 99 | — | | | | | | | | | | |
| | 1.00 | PPI | SUTAN | 6.00 | | | | | 50 | — | | | | | | | | |
| | 5.00 | PPI | SUTAN | 6.00 | | | | | 50 | — | | | | | | | | |
| 6 | 5.00 | IF | VERNAM | 1.00 | 100 | 50 | 95 | 70 | 60 | — | 95 | — | 95 | 70 | | | | |
| | 5.00 | IF | VERNAM | 6.00 | | | | | | | | | | | 85 | 10 | 60 | — |
| | 1.00 | IF | RONEET | 3.00 | 70 | — | | | | | | | | | | | | |
| | 5.00 | IF | RONEET | 3.00 | 70 | 50 | | | | | | | | | | | | |
| 7 | 5.00 | IF | VERNAM | 1.00 | 100 | 10 | 95 | 20 | 60 | — | 95 | — | 95 | 60 | | | | |
| | 4.00 | IF | VERNAM | 6.00 | | | | | | | | | | | 85 | 0 | 60 | 100 |
| | 1.00 | IF | VERNAM | 1.00 | | | 80 | 40 | | | | | | | | | | |
| | 5.00 | IF | VERNAM | 1.00 | | | 80 | 50 | | | | | | | | | | |
| | 0.50 | PPI | VERNAM | 6.00 | | | | | | | | | | | 70 | — | | |
| | 2.00 | PPI | VERNAM | 6.00 | | | | | | | | | | | 55 | — | | |
| | 1.00 | IF | VERNAM | 6.00 | | | | | | | | | | | 50 | 60 | | |
| | 1.00 | IF | RONEET | 3.00 | 70 | 10 | | | | | | | | | | | | |
| | 5.00 | IF | RONEET | 3.00 | 70 | 10 | | | | | | | | | | | | |
| | 5.00 | PES | LASSO | 3.00 | 90 | 10 | 55 | 15 | | | | | | | | | | |
| | 5.00 | PES | LASSO | 4.00 | | | | | | | | | 80 | 20 | | | | |
| 8 | 5.00 | IF | VERNAM | 1.25 | 90 | 65 | 75 | 50 | 55 | — | 90 | — | 60 | 30 | | | | |
| | 5.00 | IF | VERNAM | 6.00 | | | | | | | | | | | 90 | 0 | 60 | 100 |
| | 1.00 | IF | VERNAM | 1.00 | | | 99 | 60 | | | | | | | | | | |
| | 5.00 | IF | VERNAM | 1.00 | | | 99 | 25 | | | | | | | | | | |
| | 1.00 | IF | VERNAM | 1.25 | | | | | | | | | 85 | 20 | | | | |
| | 5.00 | IF | VERNAM | 1.25 | | | | | | | | | 85 | 20 | | | | |
| | 0.50 | PPI | VERNAM | 1.25 | | | | | | | | | 95 | 70 | | | | |
| | 1.00 | PPI | VERNAM | 1.25 | | | | | | | | | 95 | 70 | | | | |
| | 2.00 | PPI | VERNAM | 1.25 | | | | | | | | | 95 | 80 | | | | |
| | 0.05 | PPI | EPTAM | 6.00 | | | | | | | | | | | 90 | 80 | | |
| 9 | 5.00 | IF | VERNAM | 1.00 | 100 | | 20 | 95 | — | 60 | — | 95 | — | 95 | 20 | | | |
| | 5.00 | IF | VERNAM | 6.00 | | | | | | | | | | | 85 | 0 | 60 | — |
| | 1.00 | IF | VERNAM | 1.25 | | | | | | | | | 95 | 20 | | | | |
| | 5.00 | IF | VERNAM | 1.25 | | | | | | | | | 95 | 40 | | | | |
| | 0.50 | PPI | VERNAM | 1.25 | | | | | | | | | 50 | 10 | | | | |
| | 1.00 | PPI | VERNAM | 1.25 | | | | | | | | | 50 | 20 | | | | |
| | 2.00 | PPI | VERNAM | 1.25 | | | | | | | | | 50 | 20 | | | | |
| | 1.00 | IF | RONEET | 3.00 | 70 | 10 | | | | | | | | | | | | |
| | 5.00 | IF | RONEET | 3.00 | 70 | 20 | | | | | | | | | | | | |
| | 0.50 | PES | LASSO | 4.00 | | | 60 | 20 | | | | | 60 | 20 | | | | |
| | 1.00 | PES | LASSO | 4.00 | | | 60 | 0 | | | | | 60 | 10 | | | | |
| | 0.50 | PES | ANTOR | 3.00 | | | 50 | 10 | | | | | 40 | 10 | | | | |
| | 1.00 | PES | ANTOR | 3.00 | | | 50 | 0 | | | | | 40 | 0 | | | | |
| 10 | 5.00 | IF | VERNAM | 1.25 | 80 | — | 85 | 50 | 60 | — | 65 | — | 55 | 10 | | | | |
| | 5.00 | IF | VERNAM | .6.00 | | | | | | | | | | | 90 | 20 | 70 | — |
| 11 | 5.00 | IF | VERNAM | 1.25 | 100 | 60 | 100 | 50 | 60 | 50 | 100 | — | 90 | 20 | | | | |
| | 5.00 | IF | VERNAM | 6.00 | | | | | | | | | | | 95 | 75 | 60 | — |
| | 1.00 | IF | VERNAM | 1.00 | | | 99 | 20 | | | | | | | | | | |
| | 5.00 | IF | VERNAM | 1.00 | | | 99 | 50 | | | | | | | | | | |
| | 1.00 | IF | VERNAM | 1.25 | | | | | | | | | 85 | 25 | | | | |
| | 5.00 | IF | VERNAM | 1.25 | | | | | | | | | 85 | 25 | | | | |
| | 0.50 | PPI | VERNAM | 1.25 | | | | | | | | | 85 | 15 | | | | |
| | 1.00 | PPI | VERNAM | 1.25 | | | | | | | | | 85 | 10 | | | | |
| | 2.00 | PPI | VERNAM | 1.25 | | | | | | | | | 85 | 10 | | | | |

TABLE IV-continued
Effectiveness of Herbicidal Antidote

| Antidote Compound No. | Application Rate | Application Time | Herbicide Name | Herbicide Rate | Milo U | Milo T | Wheat U | Wheat T | Cotton U | Cotton T | Rice U | Rice T | Barley U | Barley T | Corn U | Corn T | Soybean U | Soybean T |
|---|---|---|---|---|---|---|---|---|---|---|---|---|---|---|---|---|---|---|
|  | 1.00 | IF | VERNAM | 1.25 |  |  |  |  | 50 | — |  |  |  |  |  |  |  |  |
|  | 5.00 | IF | VERNAM | 1.25 |  |  |  |  | 50 | — |  |  |  |  |  |  |  |  |
|  | 0.50 | PPI | VERNAM | 1.25 |  |  |  |  |  |  |  |  | 95 | 35 |  |  |  |  |
|  | 1.00 | PPI | VERNAM | 1.25 |  |  |  |  |  |  |  |  | 95 | 25 |  |  |  |  |
|  | 2.00 | PPI | VERNAM | 1.25 |  |  |  |  |  |  |  |  | 95 | 15 |  |  |  |  |
|  | 1.00 | IF | RONEET | 3.00 | 95 | 75 |  |  |  |  |  |  |  |  |  |  |  |  |
|  | 5.00 | IF | RONEET | 3.00 | 95 | 55 |  |  |  |  |  |  |  |  |  |  |  |  |
| 12 | 5.00 | IF | VERNAM | 1.25 | 90 | 80 | 75 | 40 | 55 | — | 90 | — | 60 | 40 |  |  |  |  |
|  | 5.00 | IF | VERNAM | 6.00 |  |  |  |  |  |  |  |  |  |  | 90 | 40 | 60 | 100 |
|  | 1.00 | IF | VERNAM | 1.00 |  |  | 99 | — |  |  |  |  |  |  |  |  |  |  |
|  | 5.00 | IF | VERNAM | 1.00 |  |  | 99 | 95 |  |  |  |  |  |  |  |  |  |  |
|  | 1.00 | IF | VERNAM | 1.25 |  |  |  |  |  |  |  |  | 85 | 75 |  |  |  |  |
|  | 5.00 | IF | VERNAM | 1.25 |  |  |  |  |  |  |  |  | 85 | — |  |  |  |  |
| 13 | 5.00 | IF | VERNAM | 1.25 | 100 | 30 | 95 | 30 | 70 | — | 100 | 80 | 95 | 10 |  |  |  |  |
|  | 5.00 | IF | VERNAM | 6.00 |  |  |  |  |  |  |  |  |  |  | 90 | 50 | 65 | 95 |
|  | 1.00 | IF | VERNAM | 1.00 |  |  | 99 | — |  |  |  |  |  |  |  |  |  |  |
|  | 5.00 | IF | VERNAM | 1.00 |  |  | 99 | 60 |  |  |  |  |  |  |  |  |  |  |
|  | 0.50 | PPI | VERNAM | 1.00 |  |  | 95 | — |  |  |  |  |  |  |  |  |  |  |
|  | 1.00 | PPI | VERNAM | 1.00 |  |  | 95 | — |  |  |  |  |  |  |  |  |  |  |
|  | 2.00 | PPI | VERNAM | 1.00 |  |  | 95 | 90 |  |  |  |  |  |  |  |  |  |  |
|  | 1.00 | IF | VERNAM | 1.25 |  |  |  |  |  |  |  |  | 85 | — |  |  |  |  |
|  | 5.00 | IF | VERNAM | 1.25 |  |  |  |  |  |  |  |  | 85 | — |  |  |  |  |
|  | 0.50 | PPI | VERNAM | 1.25 |  |  |  |  |  |  |  |  | 85 | — |  |  |  |  |
|  | 1.00 | PPI | VERNAM | 1.25 |  |  |  |  |  |  |  |  | 85 | — |  |  |  |  |
|  | 2.00 | PPI | VERNAM | 1.25 |  |  |  |  |  |  |  |  | 85 | — |  |  |  |  |
|  | 0.50 | PPI | VERNAM | 6.00 |  |  |  |  |  |  |  |  |  |  |  |  | 55 | — |
|  | 2.00 | PPI | VERNAM | 6.00 |  |  |  |  |  |  |  |  |  |  |  |  | 55 | — |
|  | 1.00 | IF | RONEET | 3.00 | 80 | 40 |  |  |  |  |  |  |  |  |  |  |  |  |
|  | 5.00 | IF | RONEET | 3.00 | 80 | 40 |  |  |  |  |  |  |  |  |  |  |  |  |
| 14 | 5.00 | IF | VERNAM | 1.25 | 80 | — | 85 | 50 | 60 | — | 65 | — | 55 | — |  |  |  |  |
|  | 5.00 | IF | VERNAM | 6.00 |  |  |  |  |  |  |  |  |  |  | 90 | — | 70 | — |
| 15 | 5.00 | IF | VERNAM | 1.25 | 90 | 75 | 75 | 60 | 55 | — | 90 | — | 60 | 10 |  |  |  |  |
|  | 5.00 | IF | VERNAM | 6.00 |  |  |  |  |  |  |  |  |  |  | 90 | 0 | 60 | 30 |
|  | 1.00 | IF | VERNAM | 1.25 |  |  |  |  |  |  |  |  | 85 | 30 |  |  |  |  |
|  | 5.00 | IF | VERNAM | 1.25 |  |  |  |  |  |  |  |  | 85 | 25 |  |  |  |  |
|  | 0.50 | PPI | VERNAM | 1.25 |  |  |  |  |  |  |  |  | 85 | — |  |  |  |  |
|  | 1.00 | PPI | VERNAM | 1.25 |  |  |  |  |  |  |  |  | 85 | 70 |  |  |  |  |
|  | 2.00 | PPI | VERNAM | 1.25 |  |  |  |  |  |  |  |  | 85 | 70 |  |  |  |  |
|  | 0.50 | PPI | VERNAM | 1.25 |  |  |  |  |  |  |  |  | 95 | 75 |  |  |  |  |
|  | 1.00 | PPI | VERNAM | 1.25 |  |  |  |  |  |  |  |  | 95 | 80 |  |  |  |  |
|  | 2.00 | PPI | VERNAM | 1.25 |  |  |  |  |  |  |  |  | 95 | 80 |  |  |  |  |
|  | 0.05 | PPI | EPTAM | 6.00 |  |  |  |  |  |  |  |  |  |  | 90 | 80 |  |  |
| 16 | 5.00 | IF | VERNAM | 1.25 | 80 | — | 75 | 55 | 60 | — | 85 | — | 65 | 55 |  |  |  |  |
|  | 5.00 | IF | VERNAM | 6.00 |  |  |  |  |  |  |  |  |  |  | 90 | — | 60 | 80 |
| 17 | 5.00 | IF | VERNAM | 1.25 | 90 | 65 | 75 | 60 | 55 | — | 90 | — | 60 | — |  |  |  |  |
|  | 5.00 | IF | VERNAM | 6.00 |  |  |  |  |  |  |  |  |  |  | 90 | 40 | 60 | 100 |
| 18 | 5.00 | IF | VERNAM | 1.00 | 100 | 50 | 95 | 40 | 60 | — | 95 | — | 95 | 40 |  |  |  |  |
|  | 5.00 | IF | VERNAM | 6.00 |  |  |  |  |  |  |  |  |  |  | 85 | 20 | 60 | — |
|  | 1.00 | IF | VERNAM | 1.00 |  |  | 100 | 60 |  |  |  |  |  |  |  |  |  |  |
|  | 5.00 | IF | VERNAM | 1.00 |  |  | 100 | 60 |  |  |  |  |  |  |  |  |  |  |
|  | 1.00 | IF | VERNAM | 1.25 |  |  |  |  |  |  |  |  | 95 | 20 |  |  |  |  |
|  | 5.00 | IF | VERNAM | 1.25 |  |  |  |  |  |  |  |  | 95 | 10 |  |  |  |  |
|  | 0.25 | PPI | VERNAM | 1.25 |  |  |  |  |  |  |  |  | 90 | 40 |  |  |  |  |
|  | 0.50 | PPI | VERNAM | 1.25 |  |  |  |  |  |  |  |  | 90 | 40 |  |  |  |  |
|  | 1.00 | PPI | VERNAM | 1.25 |  |  |  |  |  |  |  |  | 90 | 40 |  |  |  |  |
|  | 1.00 | PPI | VERNAM | 1.25 |  |  |  |  |  |  |  |  | 90 | 25 |  |  |  |  |
|  | 2.00 | PPI | VERNAM | 1.25 |  |  |  |  |  |  |  |  | 90 | 20 |  |  |  |  |
|  | 5.00 | PPI | VERNAM | 1.25 |  |  |  |  |  |  |  |  | 90 | 15 |  |  |  |  |
|  | 0.50 | PPI | EPTAM | 6.00 |  |  |  |  |  |  |  |  |  |  | 80 | 0 |  |  |
|  | 5.00 | PPI | EPTAM | 6.00 |  |  |  |  |  |  |  |  |  |  | 80 | 0 |  |  |
|  | 1.00 | IF | RONEET | 3.00 | 90 | 50 |  |  |  |  |  |  |  |  |  |  |  |  |
|  | 5.00 | IF | RONEET | 3.00 | 90 | 30 |  |  |  |  |  |  |  |  |  |  |  |  |
| 19 | 5.00 | IF | VERNAM | 1.25 | 100 | 40 | 95 | — | 50 | — | 95 | — | 70 | 30 |  |  |  |  |
|  | 5.00 | IF | VERNAM | 6.00 |  |  |  |  |  |  |  |  |  |  | 95 | 0 | 50 | 20 |
|  | 1.00 | IF | VERNAM | 1.25 |  |  |  |  |  |  |  |  | 95 | — |  |  |  |  |
|  | 5.00 | IF | VERNAM | 1.25 |  |  |  |  |  |  |  |  | 95 | 50 |  |  |  |  |
|  | 0.50 | PPI | EPTAM | 6.00 |  |  |  |  |  |  |  |  |  |  | 80 | 0 |  |  |
|  | 5.00 | PPI | EPTAM | 6.00 |  |  |  |  |  |  |  |  |  |  | 80 | 0 |  |  |
| 20 | 5.00 | IF | VERNAM | 1.25 | 80 | — | 85 | — | 60 | — | 65 | — | 55 | 30 |  |  |  |  |
|  | 5.00 | IF | VERNAM | 6.00 |  |  |  |  |  |  |  |  |  |  | 90 | 40 | 70 | 100 |
|  | 1.00 | IF | VERNAM | 1.25 |  |  |  |  |  |  |  |  | 90 | 85 |  |  |  |  |
|  | 5.00 | IF | VERNAM | 1.25 |  |  |  |  |  |  |  |  | 90 | 85 |  |  |  |  |
| 21 | 5.00 | IF | VERNAM | 1.00 | 100 | 60 | 95 | 50 | 60 | — | 95 | — | 90 | 40 |  |  |  |  |
|  | 5.00 | IF | VERNAM | 6.00 |  |  |  |  |  |  |  |  |  |  | 90 | 20 | 50 | 80 |
|  | 1.00 | IF | VERNAM | 1.00 |  |  | 80 | 50 |  |  |  |  |  |  |  |  |  |  |
|  | 5.00 | IF | VERNAM | 1.00 |  |  | 80 | 50 |  |  |  |  |  |  |  |  |  |  |

TABLE IV-continued

Effectiveness of Herbicidal Antidote

| Antidote Compound No. | Application Rate | Application Time | Herbicide Name | Herbicide Rate | Milo U | Milo T | Wheat U | Wheat T | Cotton U | Cotton T | Rice U | Rice T | Barley U | Barley T | Corn U | Corn T | Soybean U | Soybean T |
|---|---|---|---|---|---|---|---|---|---|---|---|---|---|---|---|---|---|---|
| 22 | 5.00 | IF | VERNAM | 1.25 | 100 | 80 | 85 | 50 | 60 | — | 100 | — | 80 | 10 | | | | |
| | 5.00 | IF | VERNAM | 6.00 | | | | | | | | | | | 90 | 20 | 60 | — |
| | 1.00 | IF | VERNAM | 1.25 | | | 80 | 40 | | | | | | | | | | |
| | 5.00 | IF | VERNAM | 1.25 | | | 80 | 10 | | | | | | | | | | |
| | 0.50 | PPI | VERNAM | 1.25 | | | | | | | | | 50 | — | | | | |
| | 1.00 | PPI | VERNAM | 1.25 | | | | | | | | | 50 | — | | | | |
| | 2.00 | PPI | VERNAM | 1.25 | | | | | | | | | 50 | — | | | | |
| | 0.50 | PPI | EPTAM | 6.00 | | | | | | | | | | | 70 | 0 | | |
| | 5.00 | PPI | EPTAM | 6.00 | | | | | | | | | | | 70 | 0 | | |
| | 0.05 | PPI | EPTAM | 6.00 | | | | | | | | | | | 90 | — | | |
| | 0.025 | PPI | EPTAM | 6.00 | | | | | | | | | | | 90 | — | | |
| | 0.0025 | PPI | EPTAM | 6.00 | | | | | | | | | | | 90 | — | | |
| | 0.05 | PPI | EPTAM | 6.00 | | | | | | | | | | | 80 | 50 | | |
| | 0.025 | PPI | EPTAM | 6.00 | | | | | | | | | | | 80 | 50 | | |
| | 0.0125 | PPI | EPTAM | 6.00 | | | | | | | | | | | 80 | 65 | | |
| 23 | 5.00 | IF | VERNAM | 1.00 | 80 | — | 80 | 40 | 70 | — | 95 | 60 | 70 | 50 | | | | |
| | 5.00 | IF | VERNAM | 6.00 | | | | | | | | | | | 90 | 0 | 50 | 90 |
| | 1.00 | IF | VERNAM | 1.00 | | | 100 | 60 | | | | | | | | | | |
| | 5.00 | IF | VERNAM | 1.00 | | | 100 | 50 | | | | | | | | | | |
| | 1.00 | PPI | VERNAM | 6.00 | | | | | | | | | | | 60 | — | | |
| | 5.00 | PPI | VERNAM | 6.00 | | | | | | | | | | | 60 | — | | |
| | 1.00 | PPI | VERNAM | 6.00 | | | | | | | | | | | 60 | 30 | | |
| | 5.00 | PPI | VERNAM | 6.00 | | | | | | | | | | | 60 | — | | |
| | 0.50 | PPI | EPTAM | 6.00 | | | | | | | | | | | 80 | 0 | | |
| | 5.00 | PPI | EPTAM | 6.00 | | | | | | | | | | | 80 | 0 | | |
| 24 | 5.00 | IF | VERNAM | 1.25 | 90 | 75 | 75 | — | 55 | — | 90 | — | 60 | 30 | | | | |
| | 5.00 | IF | VERNAM | 6.00 | | | | | | | | | | | 90 | 40 | 60 | 40 |
| | 1.00 | IF | VERNAM | 1.25 | | | | | | | | | 85 | 35 | | | | |
| | 5.00 | IF | VERNAM | 1.25 | | | | | | | | | 85 | 20 | | | | |
| | 0.50 | PPI | VERNAM | 1.25 | | | | | | | | | 95 | 75 | | | | |
| | 1.00 | PPI | VERNAM | 1.25 | | | | | | | | | 95 | 80 | | | | |
| | 2.00 | PPI | VERNAM | 1.25 | | | | | | | | | 95 | — | | | | |
| 25 | 5.00 | IF | VERNAM | 1.25 | 90 | 75 | 75 | 80 | 55 | — | 90 | 80 | 60 | 30 | | | | |
| | 5.00 | IF | VERNAM | 6.00 | | | | | | | | | | | 90 | 40 | 60 | 90 |
| | 1.00 | IF | VERNAM | 1.25 | | | | | | | | | 85 | 25 | | | | |
| | 5.00 | IF | VERNAM | 1.25 | | | | | | | | | 85 | 15 | | | | |
| | 0.50 | PPI | VERNAM | 1.25 | | | | | | | | | 95 | 75 | | | | |
| | 1.00 | PPI | VERNAM | 1.25 | | | | | | | | | 95 | 80 | | | | |
| | 2.00 | PPI | VERNAM | 1.25 | | | | | | | | | 95 | 80 | | | | |
| 26 | 5.00 | IF | VERNAM | 1.25 | 80 | — | 85 | 40 | 60 | — | 65 | 30 | 55 | 20 | | | | |
| | 5.00 | IF | VERNAM | 6.00 | | | | | | | | | | | 90 | 60 | 70 | 100 |
| | 1.00 | IF | VERNAM | 1.25 | | | | | | | 99 | — | | | | | | |
| | 5.00 | IF | VERNAM | 1.25 | | | | | | | 99 | 70 | | | | | | |
| | 1.00 | IF | VERNAM | 1.25 | | | | | | | | | 90 | 65 | | | | |
| | 5.00 | IF | VERNAM | 1.25 | | | | | | | | | 90 | 70 | | | | |
| 27 | 5.00 | IF | VERNAM | 1.00 | 100 | 80 | 95 | 60 | 60 | — | 95 | — | 95 | 50 | | | | |
| | 5.00 | IF | VERNAM | 6.00 | | | | | | | | | | | 85 | 40 | 60 | 80 |
| | 1.00 | IF | VERNAM | 1.25 | | | | | | | | | 95 | 50 | | | | |
| | 5.00 | IF | VERNAM | 1.25 | | | | | | | | | 95 | 50 | | | | |
| | 1.00 | PPI | VERNAM | 6.00 | | | | | | | | | | | 60 | — | | |
| | 5.00 | PPI | VERNAM | 6.00 | | | | | | | | | | | 60 | — | | |
| | 1.00 | PPI | VERNAM | 6.00 | | | | | | | | | | | 60 | 75 | | |
| | 5.00 | PPI | VERNAM | 6.00 | | | | | | | | | | | 60 | 80 | | |
| 28 | 5.00 | IF | VERNAM | 1.25 | 80 | — | 75 | — | 60 | — | 85 | 60 | 65 | 50 | | | | |
| | 5.00 | IF | VERNAM | 6.00 | | | | | | | | | | | 90 | 70 | 60 | 80 |
| 29 | 5.00 | IF | VERNAM | 1.25 | 100 | — | 95 | 40 | 60 | — | 100 | — | 90 | 40 | | | | |
| | 5.00 | IF | VERNAM | 6.00 | | | | | | | | | | | 85 | 50 | 70 | 90 |
| | 1.00 | IF | VERNAM | 1.00 | | | 70 | 60 | | | | | | | | | | |
| | 5.00 | IF | VERNAM | 1.00 | | | 70 | 40 | | | | | | | | | | |
| | 1.00 | IF | VERNAM | 1.25 | | | | | | | | | 85 | 45 | | | | |
| | 5.00 | IF | VERNAM | 1.25 | | | | | | | | | 85 | 20 | | | | |
| | 0.50 | PPI | VERNAM | 1.25 | | | | | | | | | 85 | — | | | | |
| | 1.00 | PPI | VERNAM | 1.25 | | | | | | | | | 85 | 80 | | | | |
| | 2.00 | PPI | VERNAM | 1.25 | | | | | | | | | 85 | 60 | | | | |
| | 0.50 | PPI | VERNAM | 6.00 | | | | | | | | | | | 60 | — | | |
| | 2.00 | PPI | VERNAM | 6.00 | | | | | | | | | | | 60 | 85 | | |
| | 0.50 | PPI | VERNAM | 6.00 | | | | | | | | | | | 55 | — | | |
| | 2.00 | PPI | VERNAM | 6.00 | | | | | | | | | | | 55 | 70 | | |
| 30 | 5.00 | IF | VERNAM | 1.25 | 100 | — | 85 | — | 60 | — | 100 | — | 80 | — | | | | |
| | 5.00 | IF | VERNAM | 6.00 | | | | | | | | | | | 90 | 40 | 60 | — |
| 31 | 5.00 | IF | VERNAM | 1.25 | 80 | 70 | 85 | 40 | 60 | — | 65 | 30 | 55 | 45 | | | | |
| | 5.00 | IF | VERNAM | 6.00 | | | | | | | | | | | 90 | 80 | 70 | — |
| | 1.00 | IF | VERNAM | 1.25 | | | | | | | 99 | 70 | | | | | | |
| | 5.00 | IF | VERNAM | 1.25 | | | | | | | 99 | 70 | | | | | | |
| | 1.00 | PPI | VERNAM | 1.00 | | | | | | | 95 | — | | | | | | |
| | 2.00 | PPI | VERNAM | 1.00 | | | | | | | 95 | — | | | | | | |

TABLE IV-continued
Effectiveness of Herbicidal Antidote

| Compound No. | Antidote Application Rate | Time | Herbicide Name | Rate | % Crop Injury Milo U | T | Wheat U | T | Cotton U | T | Rice U | T | Barley U | T | Corn U | T | Soybean U | T |
|---|---|---|---|---|---|---|---|---|---|---|---|---|---|---|---|---|---|---|
|  | 5.00 | PPI | VERNAM | 1.00 |  |  |  |  |  |  | 95 | — |  |  |  |  |  |  |
| 32 | 5.00 | IF | VERNAM | 1.25 | 90 | 80 | 100 | 85 | 70 | — | 100 | — | 75 | 30 |  |  |  |  |
|  | 5.00 | IF | VERNAM | 6.00 |  |  |  |  |  |  |  |  |  |  | 90 | 30 | 40 | 85 |
|  | 1.00 | IF | VERNAM | 1.25 | 85 | 40 |  |  |  |  |  |  |  |  |  |  |  |  |
|  | 5.00 | IF | VERNAM | 1.25 | 85 | 10 |  |  |  |  |  |  |  |  |  |  |  |  |
| 33 | 5.00 | IF | VERNAM | 1.25 | 90 | 80 | 75 | 55 | 55 | — | 90 | — | 60 | 20 |  |  |  |  |
|  | 5.00 | IF | VERNAM | 6.00 |  |  |  |  |  |  |  |  |  |  | 90 | 50 | 60 | 50 |
|  | 1.00 | IF | VERNAM | 1.00 |  |  | 99 | 60 |  |  |  |  |  |  |  |  |  |  |
|  | 5.00 | IF | VERNAM | 1.00 |  |  | 99 | 40 |  |  |  |  |  |  |  |  |  |  |
|  | 1.00 | IF | VERNAM | 1.25 |  |  |  |  |  |  |  |  | 85 | 35 |  |  |  |  |
|  | 5.00 | IF | VERNAM | 1.25 |  |  |  |  |  |  |  |  | 85 | 20 |  |  |  |  |
|  | 0.50 | PPI | VERNAM | 1.25 |  |  |  |  |  |  |  |  | 95 | 80 |  |  |  |  |
|  | 1.00 | PPI | VERNAM | 1.25 |  |  |  |  |  |  |  |  | 95 | 80 |  |  |  |  |
|  | 2.00 | PPI | VERNAM | 1.25 |  |  |  |  |  |  |  |  | 95 | 80 |  |  |  |  |
| 34 | 5.00 | IF | VERNAM | 1.25 | 90 | 65 | 75 | 60 | 55 | 40 | 90 | 80 | 60 | — |  |  |  |  |
|  | 5.00 | IF | VERNAM | 6.00 |  |  |  |  |  |  |  |  |  |  | 90 | — | 60 | — |
|  | 1.00 | IF | SUTAN | 6.00 |  |  |  |  | 60 | — |  |  |  |  |  |  |  |  |
|  | 5.00 | IF | SUTAN | 6.00 |  |  |  |  | 60 | — |  |  |  |  |  |  |  |  |

[1]Two batches of this compound were inadvertently prepared and tested, therefore, data is given for each test.

TABLE V
Effectiveness of Herbicidal Composition

| Compound No. | Antidote Application Rate | Time | Herbicide Name | Rate | % Weed Injury Watergrass U | T | Foxtail U | T | Wild oat U | T | Johnsongrass U | T | Shattercane U | T | Nutsedge U | T |
|---|---|---|---|---|---|---|---|---|---|---|---|---|---|---|---|---|
| 1 | 1.00 | IF | VERNAM | 1.00 | 90 | 60 | 70 | 60 |  |  |  |  |  |  |  |  |
|  | 5.00 | IF | VERNAM | 1.00 | 90 | 50 | 70 | 40 |  |  |  |  |  |  |  |  |
|  | 1.00 | IF | VERNAM | 1.25 |  |  | 70 | — | 100 | — |  |  |  |  |  |  |
|  | 5.00 | IF | VERNAM | 1.25 |  |  | 70 | — | 100 | — |  |  |  |  |  |  |
|  | 0.50 | PPI | VERNAM | 1.25 | 100 | — |  |  | 100 | — |  |  |  |  |  |  |
|  | 1.00 | PPI | VERNAM | 1.25 | 100 | — |  |  | 100 | — |  |  |  |  |  |  |
|  | 2.00 | PPI | VERNAM | 1.25 | 100 | — |  |  | 100 | — |  |  |  |  |  |  |
|  | 1.00 | IF | RONEET | 4.00 |  |  | 80 | — |  |  |  |  | 100 | — |  |  |
|  | 5.00 | IF | RONEET | 4.00 |  |  | 80 | — |  |  |  |  | 100 | — |  |  |
|  | 5.00 | PES | LASSO | 3.00 | 100 | — | 100 | — |  |  |  |  |  |  |  |  |
|  | 5.00 | PES | LASSO | 4.00 | 100 | — | 100 | — |  |  |  |  |  |  |  |  |
| 2 | 1.00 | IF | VERNAM | 1.00 |  |  | 70 | — | 100 | — |  |  |  |  |  |  |
|  | 5.00 | IF | VERNAM | 1.00 |  |  | 70 | 60 | 100 | — |  |  |  |  |  |  |
|  | 1.00 | IF | VERNAM | 1.00 | 90 | — | 70 | 60 |  |  |  |  |  |  |  |  |
|  | 5.00 | IF | VERNAM | 1.00 | 90 | — | 70 | 20 |  |  |  |  |  |  |  |  |
|  | 1.00 | IF | VERNAM | 1.25 |  |  | 70 | — | 100 | — |  |  |  |  |  |  |
|  | 5.00 | IF | VERNAM | 1.25 |  |  | 70 | — | 100 | — |  |  |  |  |  |  |
|  | 0.50 | PPI | VERNAM | 1.25 | 100 | — |  |  | 100 | — |  |  |  |  |  |  |
|  | 1.00 | PPI | VERNAM | 1.25 | 100 | — |  |  | 100 | — |  |  |  |  |  |  |
|  | 2.00 | PPI | VERNAM | 1.25 | 100 | — |  |  | 100 | — |  |  |  |  |  |  |
| 3 | 1.00 | IF | VERNAM | 1.00 |  |  | 70 | — | 100 | — |  |  |  |  |  |  |
|  | 5.00 | IF | VERNAM | 1.00 |  |  | 70 | — | 100 | — |  |  |  |  |  |  |
|  | 1.00 | IF | VERNAM | 1.25 |  |  | 70 | — | 100 | — |  |  |  |  |  |  |
|  | 5.00 | IF | VERNAM | 1.25 |  |  | 70 | — | 100 | — |  |  |  |  |  |  |
|  | 0.50 | PPI | VERNAM | 1.25 | 100 | — |  |  | 100 | — |  |  |  |  |  |  |
|  | 1.00 | PPI | VERNAM | 1.25 | 100 | — |  |  | 100 | — |  |  |  |  |  |  |
|  | 2.00 | PPI | VERNAM | 1.25 | 100 | — |  |  | 100 | — |  |  |  |  |  |  |
|  | 5.00 | PES | LASSO | 3.00 | 100 | — | 100 | — |  |  |  |  |  |  |  |  |
|  | 5.00 | PES | LASSO | 4.00 | 100 | — | 100 | — |  |  |  |  |  |  |  |  |
| 4 | 1.00 | IF | VERNAM | 1.25 |  |  | 70 | — | 95 | — |  |  |  |  |  |  |
|  | 5.00 | IF | VERNAM | 1.25 |  |  | 70 | — | 95 | — |  |  |  |  |  |  |
|  | 0.50 | PPI | EPTAM | 6.00 | 100 | — | 100 | — |  |  |  |  |  |  |  |  |
|  | 5.00 | PPI | EPTAM | 6.00 | 100 | — | 100 | — |  |  |  |  |  |  |  |  |
|  | 1.00 | IF | RONEET | 3.00 |  |  | 80 | — |  |  |  |  | 95 | — |  |  |
|  | 5.00 | IF | RONEET | 3.00 |  |  | 80 | — |  |  |  |  | 95 | — |  |  |
|  | 1.00 | PPI | SUTAN | 6.00 |  |  |  |  |  |  | 100 | — |  |  | 90 | — |
|  | 5.00 | PPI | SUTAN | 6.00 |  |  |  |  |  |  | 100 | — |  |  | 90 | — |
| 5[1] | 1.00 | IF | VERNAM | 1.00 | 95 | — | 80 | — |  |  |  |  |  |  |  |  |
|  | 5.00 | IF | VERNAM | 1.00 | 95 | — | 80 | — |  |  |  |  |  |  |  |  |
|  | 1.00 | PPI | SUTAN | 6.00 |  |  |  |  |  |  | 100 | — |  |  | 90 | — |
|  | 5.00 | PPI | SUTAN | 6.00 |  |  |  |  |  |  | 100 | — |  |  | 90 | — |
| 6 | 1.00 | IF | RONEET | 3.00 |  |  |  |  |  |  | 100 | — | 100 | — |  |  |
|  | 5.00 | IF | RONEET | 3.00 |  |  |  |  |  |  | 100 | — | 100 | — |  |  |
| 7 | 1.00 | IF | VERNAM | 1.00 |  |  | 70 | — | 100 | — |  |  |  |  |  |  |
|  | 5.00 | IF | VERNAM | 1.00 |  |  | 70 | — | 100 | — |  |  |  |  |  |  |
|  | 0.50 | PPI | VERNAM | 6.00 | 98 | — | 98 | — |  |  |  |  |  |  |  |  |
|  | 2.00 | PPI | VERNAM | 6.00 | 99 | — | 98 | — |  |  |  |  |  |  |  |  |
|  | 1.00 | IF | VERNAM | 6.00 | 98 | — | 95 | — |  |  |  |  |  |  |  |  |

TABLE V-continued

Effectiveness of Herbicidal Composition

| Antidote | | | | % Weed Injury | | | | | | | | | | | |
|---|---|---|---|---|---|---|---|---|---|---|---|---|---|---|---|
| Compound | Application | | Herbicide | | Watergrass | | Foxtail | | Wild oat | | Johnsongrass | | Shattercane | | Nutsedge |
| No. | Rate | Time | Name | Rate | U | T | U | T | U | T | U | T | U | T | U | T |
| | 1.00 | IF | RONEET | 3.00 | | | | | | | 100 | — | 100 | — | | |
| | 5.00 | IF | RONEET | 3.00 | | | | | | | 100 | — | 100 | — | | |
| | 5.00 | PES | LASSO | 3.00 | 100 | — | 100 | — | | | | | | | | |
| | 5.00 | PES | LASSO | 4.00 | 100 | — | 100 | — | | | | | | | | |
| 8 | 1.00 | IF | VERNAM | 1.00 | 95 | — | 80 | — | | | | | | | | |
| | 5.00 | IF | VERNAM | 1.00 | 95 | 85 | 80 | — | | | | | | | | |
| | 1.00 | IF | VERNAM | 1.25 | 90 | — | 85 | — | | | | | | | | |
| | 5.00 | IF | VERNAM | 1.25 | 90 | — | 85 | — | | | | | | | | |
| | 0.50 | PPI | VERNAM | 1.25 | 100 | — | 100 | — | | | | | | | | |
| | 1.00 | PPI | VERNAM | 1.25 | 100 | — | 100 | — | | | | | | | | |
| | 2.00 | PPI | VERNAM | 1.25 | 100 | — | 100 | — | | | | | | | | |
| | 0.05 | PPI | EPTAM | 6.00 | 100 | — | 100 | — | | | | | | | | |
| 9 | 1.00 | IF | VERNAM | 1.25 | 7 | — | 70 | — | 100 | — | | | | | | |
| | 5.00 | IF | VERNAM | 1.25 | | | 70 | — | 100 | — | | | | | | |
| | 0.50 | PPI | VERNAM | 1.25 | 100 | — | | | 100 | — | | | | | | |
| | 1.00 | PPI | VERNAM | 1.25 | 100 | — | | | 100 | — | | | | | | |
| | 2.00 | PPI | VERNAM | 1.25 | 100 | — | | | 100 | — | | | | | | |
| | 1.00 | IF | RONEET | 3.00 | | | | | | | 100 | — | 100 | — | | |
| | 5.00 | IF | RONEET | 3.00 | | | | | | | 100 | — | 100 | — | | |
| | 0.50 | PES | LASSO | 4.00 | | | | | 100 | — | | | | | | |
| | 1.00 | PES | LASSO | 4.00 | | | | | 100 | — | | | | | | |
| | 0.50 | PES | ANTOR | 3.00 | | | | | 100 | — | | | | | | |
| | 1.00 | PES | ANTOR | 3.00 | | | | | 100 | — | | | | | | |
| 11 | 1.00 | IF | VERNAM | 1.00 | 95 | — | 80 | — | | | | | | | | |
| | 5.00 | IF | VERNAM | 1.00 | 95 | — | 80 | — | | | | | | | | |
| | 1.00 | IF | VERNAM | 1.25 | 90 | — | 85 | — | | | | | | | | |
| | 5.00 | IF | VERNAM | 1.25 | 90 | — | 85 | — | | | | | | | | |
| | 0.50 | PPI | VERNAM | 1.25 | 90 | — | 90 | — | | | | | | | | |
| | 1.00 | PPI | VERNAM | 1.25 | 90 | — | 90 | — | | | | | | | | |
| | 2.00 | PPI | VERNAM | 1.25 | 90 | — | 90 | — | | | | | | | | |
| | 1.00 | IF | VERNAM | 1.25 | 90 | — | 70 | — | | | | | | | | |
| | 5.00 | IF | VERNAM | 1.25 | 90 | 75 | 70 | 45 | | | | | | | | |
| | 0.50 | PPI | VERNAM | 1.25 | 100 | — | 100 | — | | | | | | | | |
| | 1.00 | PPI | VERNAM | 1.25 | 100 | — | 100 | — | | | | | | | | |
| | 2.00 | PPI | VERNAM | 1.25 | 100 | — | 100 | — | | | | | | | | |
| | 1.00 | IF | RONEET | 3.00 | 90 | — | 90 | — | | | | | | | | |
| | 5.00 | IF | RONEET | 3.00 | 90 | — | 90 | — | | | | | | | | |
| 12 | 1.00 | IF | VERNAM | 1.00 | 95 | — | 80 | — | | | | | | | | |
| | 5.00 | IF | VERNAM | 1.00 | 95 | — | 80 | — | | | | | | | | |
| | 1.00 | IF | VERNAM | 1.25 | 90 | — | 85 | — | | | | | | | | |
| | 5.00 | IF | VERNAM | 1.25 | 90 | — | 85 | — | | | | | | | | |
| 13 | 1.00 | IF | VERNAM | 1.00 | 95 | — | 80 | — | | | | | | | | |
| | 5.00 | IF | VERNAM | 1.00 | 95 | — | 80 | — | | | | | | | | |
| | 0.50 | PPI | VERNAM | 1.00 | 95 | — | 90 | — | | | | | | | | |
| | 1.00 | PPI | VERNAM | 1.00 | 95 | — | 90 | — | | | | | | | | |
| | 2.00 | PPI | VERNAM | 1.00 | 95 | — | 90 | — | | | | | | | | |
| | 1.00 | IF | VERNAM | 1.25 | 90 | — | 85 | — | | | | | | | | |
| | 5.00 | IF | VERNAM | 1.25 | 90 | — | 85 | — | | | | | | | | |
| | 0.50 | PPI | VERNAM | 1.25 | 90 | — | 90 | — | | | | | | | | |
| | 1.00 | PPI | VERNAM | 1.25 | 90 | — | 90 | — | | | | | | | | |
| | 2.00 | PPI | VERNAM | 1.25 | 90 | — | 90 | — | | | | | | | | |
| | 0.50 | PPI | VERNAM | 6.00 | 98 | — | 100 | — | | | | | | | | |
| | 2.00 | PPI | VERNAM | 6.00 | 98 | — | 100 | — | | | | | | | | |
| | 1.00 | IF | RONEET | 3.00 | 98 | — | | | | | | | 100 | 85 | | |
| | 5.00 | IF | RONEET | 3.00 | 98 | — | | | | | | | 100 | 85 | | |
| 15 | 1.00 | IF | VERNAM | 1.25 | 90 | — | 85 | — | | | | | | | | |
| | 5.00 | IF | VERNAM | 1.25 | 90 | — | 85 | — | | | | | | | | |
| | 0.50 | PPI | VERNAM | 1.25 | 90 | — | 90 | — | | | | | | | | |
| | 1.00 | PPI | VERNAM | 1.25 | 90 | — | 90 | — | | | | | | | | |
| | 2.00 | PPI | VERNAM | 1.25 | 90 | — | 90 | — | | | | | | | | |
| | 0.50 | PPI | VERNAM | 1.25 | 100 | — | 100 | — | | | | | | | | |
| | 1.00 | PPI | VERNAM | 1.25 | 100 | — | 100 | — | | | | | | | | |
| | 2.00 | PPI | VERNAM | 1.25 | 100 | — | 100 | — | | | | | | | | |
| | 0.05 | PPI | EPTAM | 6.00 | 100 | — | 100 | — | | | | | | | | |
| 18 | 1.00 | IF | VERNAM | 1.00 | | | 70 | — | 100 | — | | | | | | |
| | 5.00 | IF | VERNAM | 1.00 | | | 70 | 20 | 100 | — | | | | | | |
| | 1.00 | IF | VERNAM | 1.25 | | | 70 | — | 100 | — | | | | | | |
| | 5.00 | IF | VERNAM | 1.25 | | | 70 | 50 | 100 | — | | | | | | |
| | 0.25 | PPI | VERNAM | 1.25 | | | 70 | — | 100 | — | | | | | | |
| | 0.50 | PPI | VERNAM | 1.25 | | | 70 | — | 100 | — | | | | | | |
| | 1.00 | PPI | VERNAM | 1.25 | | | 70 | — | 100 | — | | | | | | |
| | 1.00 | PPI | VERNAM | 1.25 | 97 | — | 97 | — | | | | | | | | |
| | 2.00 | PPI | VERNAM | 1.25 | 97 | — | 97 | — | | | | | | | | |
| | 5.00 | PPI | VERNAM | 1.25 | 97 | — | 97 | — | | | | | | | | |
| | 0.50 | PPI | EPTAM | 6.00 | 100 | — | 100 | — | | | | | | | | |
| | 5.00 | PPI | EPTAM | 6.00 | 100 | — | 100 | — | | | | | | | | |
| | 1.00 | IF | RONEET | 3.00 | 95 | — | | | | | | | 100 | — | | |

TABLE V-continued

Effectiveness of Herbicidal Composition

| Antidote | | | | | | | | | | | | | | | |
|---|---|---|---|---|---|---|---|---|---|---|---|---|---|---|---|
| Compound | Application | | Herbicide | | \multicolumn{10}{c|}{% Weed Injury} |
| | Rate | Time | Name | Rate | Watergrass | | Foxtail | | Wild oat | | Johnsongrass | | Shattercane | | Nutsedge | |
| No. | | | | | U | T | U | T | U | T | U | T | U | T | U | T |
| | 5.00 | IF | RONEET | 3.00 | 95 | — | | | | | | | 100 | — | | |
| 19 | 1.00 | IF | VERNAM | 1.25 | | | 70 | — | 100 | — | | | | | | |
| | 5.00 | IF | VERNAM | 1.25 | | | 70 | — | 100 | — | | | | | | |
| | 0.50 | PPI | EPTAM | 6.00 | 100 | — | 100 | — | | | | | | | | |
| | 5.00 | PPI | EPTAM | 6.00 | 100 | — | 100 | — | | | | | | | | |
| 20 | 1.00 | IF | VERNAM | 1.25 | 95 | — | 80 | — | | | | | | | | |
| | 5.00 | IF | VERNAM | 1.25 | 95 | — | 80 | — | | | | | | | | |
| 21 | 1.00 | IF | VERNAM | 1.00 | | | 70 | — | 100 | — | | | | | | |
| | 5.00 | IF | VERNAM | 1.00 | | | 70 | — | 100 | — | | | | | | |
| 22 | 1.00 | IF | VERNAM | 1.25 | | | 70 | — | 100 | — | | | | | | |
| | 5.00 | IF | VERNAM | 1.25 | | | 70 | — | 100 | — | | | | | | |
| | 0.50 | PPI | VERNAM | 1.25 | 100 | — | | | 100 | — | | | | | | |
| | 1.00 | PPI | VERNAM | 1.25 | 100 | — | | | 100 | — | | | | | | |
| | 2.00 | PPI | VERNAM | 1.25 | 100 | — | | | 100 | — | | | | | | |
| | 0.50 | PPI | EPTAM | 6.00 | 100 | — | 100 | — | | | | | | | | |
| | 5.00 | PPI | EPTAM | 6.00 | 100 | — | 100 | — | | | | | | | | |
| | 0.05 | PPI | EPTAM | 6.00 | 95 | — | 95 | — | | | | | | | | |
| | 0.025 | PPI | EPTAM | 6.00 | 95 | — | 95 | — | | | | | | | | |
| | 0.0025 | PPI | EPTAM | 6.00 | 95 | — | 95 | — | | | | | | | | |
| | 0.05 | PPI | EPTAM | 6.00 | 100 | — | 100 | — | | | | | | | | |
| | 0.025 | PPI | EPTAM | 6.00 | 100 | — | 100 | — | | | | | | | | |
| | 0.0125 | PPI | EPTAM | 6.00 | 100 | — | 100 | — | | | | | | | | |
| 23 | 1.00 | IF | VERNAM | 1.00 | | | 70 | — | 100 | — | | | | | | |
| | 5.00 | IF | VERNAM | 1.00 | | | 70 | — | 100 | — | | | | | | |
| | 1.00 | PPI | VERNAM | 6.00 | 100 | — | 100 | — | | | | | | | | |
| | 5.00 | PPI | VERNAM | 6.00 | 100 | — | 100 | — | | | | | | | | |
| | 1.00 | PPI | VERNAM | 6.00 | 85 | — | 90 | — | | | | | | | | |
| | 5.00 | PPI | VERNAM | 6.00 | 85 | — | 90 | — | | | | | | | | |
| | 0.50 | PPI | EPTAM | 6.00 | 100 | — | 100 | — | | | | | | | | |
| | 5.00 | PPI | EPTAM | 6.00 | 100 | — | 100 | — | | | | | | | | |
| 24 | 1.00 | IF | VERNAM | 1.25 | 90 | — | 85 | — | | | | | | | | |
| | 5.00 | IF | VERNAM | 1.25 | 90 | — | 85 | — | | | | | | | | |
| | 0.50 | PPI | VERNAM | 1.25 | 100 | — | 100 | — | | | | | | | | |
| | 1.00 | PPI | VERNAM | 1.25 | 100 | — | 100 | — | | | | | | | | |
| | 2.00 | PPI | VERNAM | 1.25 | 100 | — | 100 | — | | | | | | | | |
| 25 | 1.00 | IF | VERNAM | 1.25 | 90 | — | 85 | — | | | | | | | | |
| | 5.00 | IF | VERNAM | 1.25 | 90 | — | 85 | 75 | | | | | | | | |
| | 0.50 | PPI | VERNAM | 1.25 | 100 | — | 100 | — | | | | | | | | |
| | 1.00 | PPI | VERNAM | 1.25 | 100 | — | 100 | — | | | | | | | | |
| | 2.00 | PPI | VERNAM | 1.25 | 100 | — | 100 | — | | | | | | | | |
| 26 | 1.00 | IF | VERNAM | 1.25 | 95 | — | 80 | — | | | | | | | | |
| | 5.00 | IF | VERNAM | 1.25 | 95 | 80 | 80 | 70 | | | | | | | | |
| | 1.00 | IF | VERNAM | 1.25 | 95 | — | 80 | — | | | | | | | | |
| | 5.00 | IF | VERNAM | 1.25 | 95 | — | 80 | — | | | | | | | | |
| 27 | 1.00 | IF | VERNAM | 1.25 | | | 70 | — | 100 | — | | | | | | |
| | 5.00 | IF | VERNAM | 1.25 | | | 70 | — | 100 | — | | | | | | |
| | 1.00 | PPI | VERNAM | 6.00 | 100 | — | 100 | — | | | | | | | | |
| | 5.00 | PPI | VERNAM | 6.00 | 100 | — | 100 | — | | | | | | | | |
| | 1.00 | PPI | VERNAM | 6.00 | 85 | — | 90 | — | | | | | | | | |
| | 5.00 | PPI | VERNAM | 6.00 | 85 | — | 90 | — | | | | | | | | |
| 29 | 1.00 | IF | VERNAM | 1.00 | | | 50 | — | 100 | — | | | | | | |
| | 5.00 | IF | VERNAM | 1.00 | | | 50 | — | 100 | — | | | | | | |
| | 1.00 | IF | VERNAM | 1.25 | 60 | — | | | 100 | — | | | | | | |
| | 5.00 | IF | VERNAM | 1.25 | 60 | — | | | 100 | — | | | | | | |
| | 0.50 | PPI | VERNAM | 1.25 | 90 | — | 90 | — | | | | | | | | |
| | 1.00 | PPI | VERNAM | 1.25 | 90 | — | 90 | — | | | | | | | | |
| | 2.00 | PPI | VERNAM | 1.25 | 90 | — | 90 | — | | | | | | | | |
| | 0.50 | PPI | VERNAM | 6.00 | 100 | — | 100 | — | | | | | | | | |
| | 2.00 | PPI | VERNAM | 6.00 | 100 | — | 100 | — | | | | | | | | |
| | 0.50 | PPI | VERNAM | 6.00 | 98 | — | 100 | — | | | | | | | | |
| | 2.00 | PPI | VERNAM | 6.00 | 98 | — | 100 | — | | | | | | | | |
| 31 | 1.00 | IF | VERNAM | 1.25 | 95 | 60 | 80 | 60 | | | | | | | | |
| | 5.00 | IF | VERNAM | 1.25 | 95 | — | 80 | 70 | | | | | | | | |
| | 1.00 | PPI | VERNAM | 1.00 | 95 | — | 80 | — | | | | | | | | |
| | 2.00 | PPI | VERNAM | 1.00 | 95 | — | 80 | — | | | | | | | | |
| | 5.00 | PPI | VERNAM | 1.00 | 95 | — | 80 | — | | | | | | | | |
| 32 | 1.00 | IF | VERNAM | 1.25 | 90 | — | 85 | — | | | | | | | | |
| | 5.00 | IF | VERNAM | 1.25 | 90 | — | 85 | — | | | | | | | | |
| 33 | 1.00 | IF | VERNAM | 1.00 | 95 | — | 80 | — | | | | | | | | |
| | 5.00 | IF | VERNAM | 1.00 | 95 | 85 | 80 | 75 | | | | | | | | |
| | 1.00 | IF | VERNAM | 1.25 | 90 | — | 85 | — | | | | | | | | |
| | 5.00 | IF | VERNAM | 1.25 | 90 | — | 85 | — | | | | | | | | |
| | 0.50 | PPI | VERNAM | 1.25 | 100 | — | 100 | — | | | | | | | | |
| | 1.00 | PPI | VERNAM | 1.25 | 100 | — | 100 | — | | | | | | | | |
| | 2.00 | PPI | VERNAM | 1.25 | 100 | — | 100 | — | | | | | | | | |
| 34 | 1.00 | IF | SUTAN | 6.00 | 100 | — | 100 | — | | | | | | | | |

TABLE V-continued

| | Antidote | | | | Effectiveness of Herbicidal Composition | | | | | | | | | | |
|---|---|---|---|---|---|---|---|---|---|---|---|---|---|---|---|
| | | | | | | | | | % Weed Injury | | | | | | |
| Compound | Application | | Herbicide | | Watergrass | | Foxtail | | Wild oat | | Johnsongrass | | Shattercane | | Nutsedge | |
| No. | Rate | Time | Name | Rate | U | T | U | T | U | T | U | T | U | T | U | T |
| | 5.00 | IF | SUTAN | 6.00 | 100 | — | 100 | — | | | | | | | | |

[1]Two batches of this compound were inadvertently prepared and tested, therefore, data is given for each test.

Test Results

The compounds of this invention showed good antidotal activity for the protection of corn, milo, wheat, and barley from thiocarbamate and acetanilide herbicides. Some of the compounds showed activity on rice. There was little protection of cotton. Unfortunately, many of the compounds exacerbated soybean injuries. The compounds did not diminish herbicidal effectiveness.

Although application may be made at any of the stages of growth previously discussed, the preferred methods of application are in-furrow and pre-plant incorporation. The antidote compound may be applied either separately or combined with the herbicide as a part of a two-part herbicidal system.

Formulations

The compounds and compositions can be formulated in the same manner in which herbicides are generally formulated. The object of the formulation is to apply the compounds and composition to the loci where control is desired by a convenient method. The "loci" may include soil, seeds, seedlings, and vegetation.

Formulations will generally contain several additives. Among these are some inert ingredients and diluent carriers such as organic solvents, water, oil and water, water in oil emulsions, carriers or dusts and granules, and surface active wetting, dispersing and emulsifying agents.

Fertilizers, e.g., ammonium nitrate, urea and superphosphate, may also be added.

Aids to rooting and growth, e.g., compost, manure, humus, sand, etc. may likewise be added.

The formulations are commonly dusts, wettable powders, granules, solutions of emulsifiable concentrates.

Dusts are free-flowing powder compositions containing the herbicidal compound impregnated on a particulate carrier. The particle size of the carriers is usually in the approximate range of 30 to 50 microns. Examples of suitable carriers are talc, bentonite, diatomaceous earth, and pyrophyllite. Anti-caking and antistatic agents can be added, if desired. The composition generally contains up to 50% of active ingredient. Dusts, like liquid compositions, can be applied by spraying from boom and hand sprayers or airplanes.

Wettable powders are finely divided compositions comprising a particular carrier impregnated with the herbicidal compound and additionally containing one or more surface active agents. The surface active agent promotes rapid dispersion of the powder in aqueous medium to form stable, sprayable suspensions. A wide variety of surface active agents can be used, for example, long chain fatty alcohols and alkali metal salts of the sulfated fatty alcohols; salts of sulfonic acid; esters of long chain fatty acids; and polyhydric alcohols, in which the alcohol groups are free, omega-substituted polyethylene glycols of relatively long chain length. A list of surface active agents suitable for use in agriculture formulations can be found in Wade Van Valkenburg, *Pesticide Formulations* (Marcel Dekker, Inc., N.Y., 1973) at pages 79–84.

Granules comprise the herbicidal composition impregnated on a particular inert carrier having a particle size of about 1 to 2 millimeters in diameter. The granules can be made by spraying a solution of the active ingredient in a volatile solvent onto the granular carrier. Suitable carriers in preparation of granules include clay, vermiculite, sawdust, granular carbon etc.

The herbicidal compositions can also be applied to the soil in the form of a solution in a suitable solvent. Solvents frequently used in herbicidal formulations include kerosene, fuel oil, xylene, petroleum fractions with boiling ranges above xylene, and aromatic petroleum fractions rich in methylated naphthalenes.

Emulsifiable concentrates consist of an oil solution of the herbicide along with an emulsifying agent. Prior to use the concentrate is diluted with water to form a suspended emulsion of oil droplets. The emulsifiers used are usually a mixture of anionic and nonionic surfactants. Other additives such as spreading agents and stickers can be included in the emulsifiable concentrate.

The compounds and compositions of this invention can also be supplied by addition to irrigation water supplied to the field to be treated. This method of application permits the penetration of the compositions into the soil as the water is absorbed therein.

It is not necessary that the compounds and compositions be admixed with the soil particles. After application by the above discussed methods, they may be distributed below the surface to a depth of at least one-half inch by conventional means such as discing, dragging, or mixing.

What is claimed:

1. A two-part herbicidal composition comprised of
  (a) non-phytotoxic effective amount of an α-halo-Ω-haloalkylamide compound of the formula

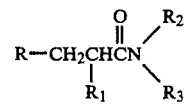

in which
R is selected from the group consisting of chlorine and bromine;
$R_1$ is selected from the group consisting of chlorine and bromine, provided that it is different from R;
$R_2$ is selected from the group consisting of hydrogen and methyl; and
$R_3$ is selected from the group consisting of methoxy substituted cyanoalkyl having 2 to 10 carbon atoms, and cyanocycloalkyl having 5 to 14 carbon atoms; and
  (b) an herbicidally effective amount of a thiocarbamate herbicide of the formula

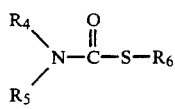

in which

R$_4$ is selected from the group consisting of 1 to 6 carbon alkyl and 2-6 carbon alkenyl;

R$_5$ is selected from the group consisting of 1 to 6 carbon alkyl, 2 to 6 carbon alkenyl, cyclohexyl, and phenyl; or R$_4$ and R$_5$ taken together with the nitrogen atom to which they are attached form an alkylene ring; and R$_6$ is selected from the group consisting of 1 to 6 carbon alkyl, 1 to 6 carbon haloalkyl, 4 to 10 carbon alkylene ring, phenyl and benzyl.

2. A composition according to claim 1 in which R is chloro, R$_1$ is bromo, R$_2$ is hydrogen, and R$_3$ is cyanocycloalkyl.

3. A composition according to claim 2 in which R$_3$ is 1-cyclopentane carbonitrilo.

4. A composition according to claim 2 in which R$_3$ is 1-cyclopentylacetonitrilo.

5. A composition according to claim 2 in which R$_3$ is 1-cyanocyclohexyl.

6. A composition according to claim 2 in which R$_3$ is 4-methylcyclohexylcarbonitrilo.

7. A composition according to claim 2 in which R$_3$ is 1-cyano-4-ethylcyclohexyl.

8. A composition according to claim 2 in which R$_3$ is 1-cyano-4-t-butylcyclohexyl.

9. A composition according to claim 2 in which R$_3$ is 1-cyano-4-t-pentylcyclohexyl.

10. A composition according to claim 2 in which R$_3$ is 1-cyanocycloheptyl.

11. A composition according to claim 2 in which R$_3$ is 1-cyanocyclooctyl.

12. A composition according to claim 1 in which R is bromo, R$_1$ is chloro, R$_2$ is hydrogen, and R$_3$ is cyanocycloalkyl.

13. A composition according to claim 12 in which R$_3$ is 1-cyanocyclohexyl.

14. A composition according to claim 12 in which R$_3$ is 1-cyano-4-methylcyclohexyl.

15. A composition according to claim 12 in which R$_3$ is 1-cyanocyclooctyl.

* * * * *